United States Patent
Tambe et al.

(10) Patent No.: US 9,714,932 B2
(45) Date of Patent: Jul. 25, 2017

(54) MONOLAYER STRESS MICROSCOPY

(75) Inventors: Dhananjay T. Tambe, Brighton, MA (US); Jeffrey J. Fredberg, Sharon, MA (US); James Butler, Brookline, MA (US); Xavier Trepat, Barbera del Valles (ES)

(73) Assignee: President and Fellows of Harvard College, Cambridge, MA (US)

(*) Notice: Subject to any disclaimer, the term of this patent is extended or adjusted under 35 U.S.C. 154(b) by 783 days.

(21) Appl. No.: 14/110,936

(22) PCT Filed: Apr. 13, 2012

(86) PCT No.: PCT/US2012/033450
§ 371 (c)(1),
(2), (4) Date: Jan. 14, 2014

(87) PCT Pub. No.: WO2012/142366
PCT Pub. Date: Oct. 18, 2012

(65) Prior Publication Data
US 2014/0212909 A1    Jul. 31, 2014

Related U.S. Application Data

(60) Provisional application No. 61/476,122, filed on Apr. 15, 2011.

(51) Int. Cl.
*G01N 33/483*    (2006.01)
*G06T 7/246*    (2017.01)
*G06K 9/00*    (2006.01)

(52) U.S. Cl.
CPC ....... *G01N 33/4833* (2013.01); *G06K 9/0014* (2013.01); *G06K 9/00134* (2013.01); *G06T 7/246* (2017.01); *G06T 2207/10056* (2013.01); *G06T 2207/30024* (2013.01); *G06T 2207/30204* (2013.01)

(58) Field of Classification Search
None
See application file for complete search history.

(56) References Cited

FOREIGN PATENT DOCUMENTS

RU    2361215 C1    7/2009
WO    WO-2009154688 A1    12/2009

OTHER PUBLICATIONS

Roure et al., Force mapping in epithelial cell migration, PNAS, pp. 2390-2395, vol. 102, No. 7, 2005.*
Angelini, Cell Migration Driven by Cooperative Substrate Deformation Patterns, Physical Review Letters, 104, 168104 (2010).*
Trepat, Physical forces during collective cell migration, Nature Physics, vol. 5, Jun. 2009.*
Liu et al. "Mechanical Tugging Force Regulates the Size of Cell-Cell Junctions." *PNAS*. 107.22(2010):9944-9949.
Maruthamuthu et al. "Cell-ECM Traction Force Modulates Endogenous Tension at Cell-Cell Contacts." *PNAS*. 108.12(2011):4708-4713.
Tambe et al. "Collective Cell Guidance by Cooperative Intercelluar Forces." *Nat. Mater.* 10.6(2011):469-475.
Trepat et al. "Physical Forces During Collective Cell Migration." *Nat. Physics.* 5(2009):426-430.
Wang et al. "Cell Traction Force and Measurement Methods." *Biomechan. Model Mechanobiol.* 6(2007):361-371.

* cited by examiner

*Primary Examiner* — Taeyoon Kim
*Assistant Examiner* — Srikanth Patury
(74) *Attorney, Agent, or Firm* — Mintz Levin Cohn Ferris Glovsky and Popeo, P.C.

(57) ABSTRACT

Disclosed are systems, apparatus, devices and methods, including a method that includes determining traction forces exerted by a cellular monolayer on a substrate on which the monolayer is placed, and determining internal forces within and between cells of the monolayer based on the determined traction forces. In some embodiments, determining the internal forces of the cellular monolayer may include determining internal stresses within the cellular monolayer that act to balance the determined traction forces over at least part of the cellular monolayer. In some embodiments, determining of the internal stresses may also include setting boundary conditions at a boundary determined based on an optical field of view of an observed section of the monolayer.

13 Claims, 20 Drawing Sheets

| CELL CULTURE. |
|---|
| *Cell culture:* All the cells were cultured on plastic flasks and incubated at 37°C with 5% $CO_2$. |
| *Cell seeding:* A 4µl drop of dense cell solution (8 million cells/ml) was gently suspended on the center of the gel containing 2ml media. The cells were then kept at 37°C and 5% $CO_2$ for 48 hours to form confluent circular monolayer that migrates radially outwards. |
| *Preparation of polyacrylamide gel substrates:* Polyacrylamide substrate preparation was similar to published protocol. |

| Cells | Medium |
|---|---|
| Madin-Darby canine kidney cells (MDCK) (strain II) | Modified Eagle's medium (MEM) with Earle's salts supplemented with 5% fetal bovine serum (FBS), 2mM l-glutamine, 100U/ml penicillin, and 100 g/ml streptomycin |
| Rat pulmonary microvascular endothelial cells (RPMEC) | Roswell Park Memorial Institute (RPMI-1640) supplemented with 10% FBS, 100 U/ml penicillin and, 100 g/ml streptomycin, and Fungizone [3]. |
| MCF10A with overexpressing ErbB2 MCF10A with overexpressing HA-tagged 14-3-3ζ MCF10A control (vector) | Dulbecco's modified Eagle's medium (DMEM)/F12 supplemented with 5% donor horse serum, 20 ng/ml epidermal growth factor (EGF), 10 lg/ml insulin, 0.5 lg/ml hydrocortisone, 100 ng/ml cholera toxin, and antibiotics [4] |

FIG. 15

MONOLAYER STRESS MICROSCOPY

RELATED APPLICATIONS

This application is a national stage application, filed under 35 U.S.C. §371, of International Application No. PCT/US2012/033450 filed Apr. 13, 2012, which claims the benefit of priority under 35 U.S.C. §119(e) to U.S. Provisional Application No. 61/476,122 filed Apr. 15, 2011, the entire contents of each are incorporated herein by reference in their entirety.

BACKGROUND

The present disclosure is directed to monolayer stress microscopy, and more particularly to determination of cellular monolayer stress forces (for example, based on determination of traction forces exerted by the cellular monolayer on a substrate on which the cellular monolayer is placed) using monolayer stress microscopy.

A variety of fundamental processes in development, health, and disease depend upon the coordinated motion of cell groups. Conventionally, to describe coordinated cellular motions in these processes, high-throughput genomic approaches have identified molecular players and mapped their interaction into comprehensive signaling networks. But even with detailed signaling and structural information in hand, the role of intercellular adhesion in collective migration is disputed, and understanding of collective cellular migration lacks predictive power and remains largely descriptive. Central to these limitations is the absence of a physical picture that links cell motion to mechanical stresses exerted within the cell body and at cell-cell boundaries, for these stresses have never before been measured. Indeed, some studies have concluded that calculating forces across multiple cell-cell contacts is mathematically insoluble (Z. Liu et al., "Mechanical tugging force regulates the size of cell-cell junctions," *Proc Natl Acad Sci USA* 107, 9944 (Jun. 1, 2010)).

SUMMARY

Described herein are high resolution maps of stress components within an advancing monolayer sheet, and systems and procedures to generate such maps. These stress maps reveal that local cellular trajectory follows local stress fields that are severely heterogeneous and dramatically cooperative over distances spanning many cell bodies. Together, these findings reveal an unanticipated but unifying physiological principle, namely, that each cell tends to migrate and remodel so as to maintain minimal local intercellular shear stress. Detailed knowledge of the biology of the cell-cell junction, the cryptic lamellipodium (see Supplement 7 of Exhibit B), or any specific molecular event do not predict such a unifying principle because it is an emergent property of a multicellular collective system. By analogy to the well known guidance mechanisms of chemotaxis, durotaxis and haptotaxis, this distinct but innately collective mechanism is referred to as plithotaxis, from the Greek "plithos" denoting crowd, swarm, or throng.

Thus, in one aspect, a method is disclosed. The method includes determining traction forces exerted by a cellular monolayer on a substrate on which the monolayer is placed, and determining internal forces within and between cells of the monolayer based on the determined traction forces.

Embodiments of the method may include any of the features described in the present disclosure, as well as any one or more of the following features.

Determining the internal forces of the cellular monolayer based on the determined traction forces may include determining internal stresses within the cellular monolayer that act to balance the determined traction forces over at least part of the cellular monolayer.

Determining the internal stresses that act to balance the determined traction forces over the at least part of the monolayer may include determining the internal stresses resulting from imposing mechanical equilibrium of forces according to $\sigma_{ij,i}=T_i$, where $\sigma_{ij}$ represents internal stress within the cellular monolayer, and at a same position, $T_i$ represents a traction force exerted by the cells on the substrate. The determining of the internal stresses may also include setting boundary conditions at a boundary determined based on an optical field of view of an observed section of the monolayer, determining errors associated with the setting of the boundary conditions, and identifying an inner region where the determined errors are smaller than a pre-determined error threshold.

Setting the boundary conditions at the boundary determined based on the optical field of view may include setting the boundary conditions along the optical field of view when a region within the boundary does not include a free edge of the monolayer, and setting the boundary conditions along an edge defined by sides of a group of cells that do not abut sides of another group of cells from the monolayer when the optical field of view includes free edges of the monolayer.

Setting the boundary conditions may include setting the boundary conditions at the boundary to have one or more of, for example, a zero normal displacement, zero stress, and/or any given relationship between displacement and stress.

Determining the internal stresses resulting from imposing mechanical equilibrium of the forces according to $\sigma_{ij,i}=T_i$ may include performing one or more numerical techniques to solve equations of the mechanical equilibrium over a mathematical representation of the at least part of the cellular monolayer subjected to the traction forces using boundary conditions set along one or more of, for example, the optical field of view, and free edges of the monolayer.

Determining the traction forces may include determining deformations of the substrate caused by the cellular monolayer, and determining the traction forces based on the determined deformations in the substrate.

Determining the substrate deformation may include measuring the substrate deformation based on an acquired image pair, the image pair including one image of surface makers integrated with a surface of the substrate when the monolayer is placed on the substrate, and another image of the surface markers with the monolayer removed from the substrate, and may also include determining drift between of the surface markers based on the acquired image pair, and determining the deformations of the substrate at the surface based on data of the acquired image pair and based on the determined drift.

Determining deformations of the substrate may include applying a numerical technique to the drift corrected image pair to obtain the deformations of the substrate at the surface. Applying the numerical technique may include applying a cross-correlation numerical technique to the drift correct image pair.

Determining the drift may include performing an a priori drift-correction technique based on fixed markers that are not displaced by deformations of the substrate due to the cellular monolayer.

Determining the traction forces based on the determined deformations in the substrate may include performing a traction microscopy procedure on data representative of the deformations in the substrate caused by the traction forces exerted by the cellular monolayer on the substrate to determine the traction forces.

Performing the traction microscopy procedure may include applying a Fourier-Transform-based procedure to transform the deformations of the substrate into tractions on a surface of the substrate.

The cellular monolayer may include a planar group of cells that are attached to each other and have structural arrangements ranging from cells in a single layer with only one cell surrounded by other cells on all sides and all the cells adherent to the substrate, to cells forming multiple layers with many cells surrounded by other cells from all sides and the bottom layer adherent to the substrate.

The substrate may include a deformable substrate including markers integrated with its surface.

The deformable substrate may include collagen-coated polyacrylamide gels with fluorescent beads underneath a surface of the gel.

In another aspect, a method is disclosed. The method includes determining traction forces exerted by a cellular monolayer on a substrate on which the monolayer is placed, and determining internal forces within and between cells of the monolayer based on the determined traction forces, including setting boundary conditions at a boundary determined based on an optical field of view of an observed section of the monolayer.

Embodiments of the method may include any of the features described in the present disclosure, including any of the features described above in relation to the first method.

In yet another aspect, a system is disclosed. The system includes a microscope to acquire data needed to determine traction forces exerted by a cellular monolayer on a substrate, at least one processor-based device, and at least one non-transitory storage device to store computer instructions. The computer instructions include instructions that when executed on the at least one processor-based device cause the at least one processor-based device to determine based on the acquired data the traction forces exerted by the cellular monolayer on the substrate on which the monolayer is placed, and determine internal forces within and between the cells of the monolayer based on the determined traction forces.

Embodiments of the system may include any of the features described in the present disclosure, including any of the features described above in relation to the methods, as well as any one of the following features.

The computer instructions that cause the at least one processor based device to determine the internal forces based on the determined traction forces may include computer instructions that cause the at least one processor-based device to determine internal stresses within the cellular monolayer that act to balance the determined traction forces over at least part of the cellular monolayer.

The computer instructions that cause the at least one processor based device to determine the internal stresses that act to balance the determined traction forces over the at least part of the monolayer may include computer instructions that cause the at least one processor-based device to determine the internal stress resulting from imposing mechanical equilibrium of forces according to $\sigma_{ij,i}=T_i$, where $\sigma_{ij}$ represents internal stress within the cellular monolayer, and at a same position, $T_i$ represents a traction force exerted by the cells on the substrate. The computer instructions may also include instructions to cause the at least one processor-based device to set boundary conditions at a boundary determined based on an optical field of view of an observed section of the monolayer, determine errors associated with the setting of the boundary conditions, and identify an inner region where those errors are smaller than a pre-determined error threshold.

The system may further include an image capturing device to capture images of surface markers and images of the monolayer. The deformable substrate may include the surface markers integrated on a surface of the substrate, and the computer instructions may further include instructions to facilitate data acquisition of drift-corrected data from the microscope by computing a parameter to quantify alignment of fixed markers to determine adjustment of x-, y-, and z-focus for acquiring a drift-corrected second image of the image pair that represents deformations of the substrate. The parameter to quantify alignment of two images of the fixed markers may be root mean square of a difference in intensities of corresponding pixels from the two images.

In an additional aspect, a diagnostic method is disclosed. The method includes placing a cellular monolayer sample on a substrate, determining traction forces exerted by the cellular monolayer sample on the substrate, determining internal forces within and between cells of the cellular monolayer based on the determined traction forces, and performing, based at least in part on the determined internal forces, a diagnostic procedure for the cellular monolayer sample to identify at least one condition in relation to the cellular monolayer sample, the at least one condition including one or more of, for example, a cancerous condition, a vascular injury, a bladder dysfunction, and/or dysfunction of any barrier system in any monolayer.

Embodiments of the method may include any of the features described in the present disclosure, including any of the features described above in relation to the methods and system, as well as the following feature.

Performing, based at least in part on the determined internal forces, the diagnostic procedure for the cellular monolayer sample may include performing a comparison of data representative of the determined internal forces within and between the cells of the cellular monolayer sample to data representative of determined internal forces within and between cells of a healthy cellular monolayer specimen, and making a diagnosis of an existence of the at least one condition based on the comparison.

In a further aspect, a method for drug screening is disclosed. The method includes placing on a substrate a cellular monolayer sample, determining traction forces exerted on the substrate by the cellular monolayer sample, determining internal forces within and between cells of the cellular monolayer sample based on the determined traction forces, performing a comparison of data representative of the determined internal forces within and between the cells of the cellular monolayer sample to data representative of determined internal forces within and between cells of a cellular monolayer specimen known to include a specified therapeutic substance, and determining whether the specified therapeutic substance is present in the cellular monolayer sample based on the comparison of data representative of the determined internal forces within and between cells of the cellular monolayer sample to data representative of determined internal forces within and between the cells of the cellular monolayer specimen known to include the specified therapeutic substance.

Embodiments of the method may include any of the features described in the present disclosure, including any of the features described above in relation to the methods and system.

In an additional aspect, a method for identifying an inhibitor of metastasis is disclosed. The method includes providing on a substrate a cellular monolayer sample, determining traction forces exerted on the substrate by the cellular monolayer sample in the presence of a candidate compound, determining internal forces within and between cells of the cellular monolayer sample based on the determined traction forces, and comparing a first measure of determined internal forces within and between the cells of the cellular monolayer sample in the presence of said candidate compound to a second measure of determined internal forces within and between cells of a cellular monolayer specimen in the absence of said candidate compound, wherein an alteration in the level of internal forces in the presence of said candidate compound compared to the absence of said candidate compound indicates that said compound inhibits metastasis.

Embodiments of the method may include any of the features described in the present disclosure, including any of the features described above in relation to the methods and system.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

These and other aspects will now be described in detail with reference to the following drawings.

FIG. 15 is a table listing and describing several cell cultures.

Like reference symbols in the various drawings indicate like elements.

DETAILED DESCRIPTION

Disclosed are methods, systems, apparatus and devices, including a method that includes determining traction forces exerted by a cellular monolayer on a substrate (e.g., an adherent substrate) on which the cellular monolayer is placed (disposed), and determining internal forces within and between cells of a cellular monolayer (such internal forces are also referred to as intercellular forces) based on the determined traction forces. In some embodiments, determining the intercellular forces based on the determined traction forces may include determining internal stresses (e.g., internal mechanical stresses) within the cellular monolayer that act to balance the determined traction forces over at least part of, and in some embodiment, over the entirety of, the cellular monolayer. Determining the internal stresses may include setting boundary conditions at a boundary determined based on an optical field of view.

Figure 1:
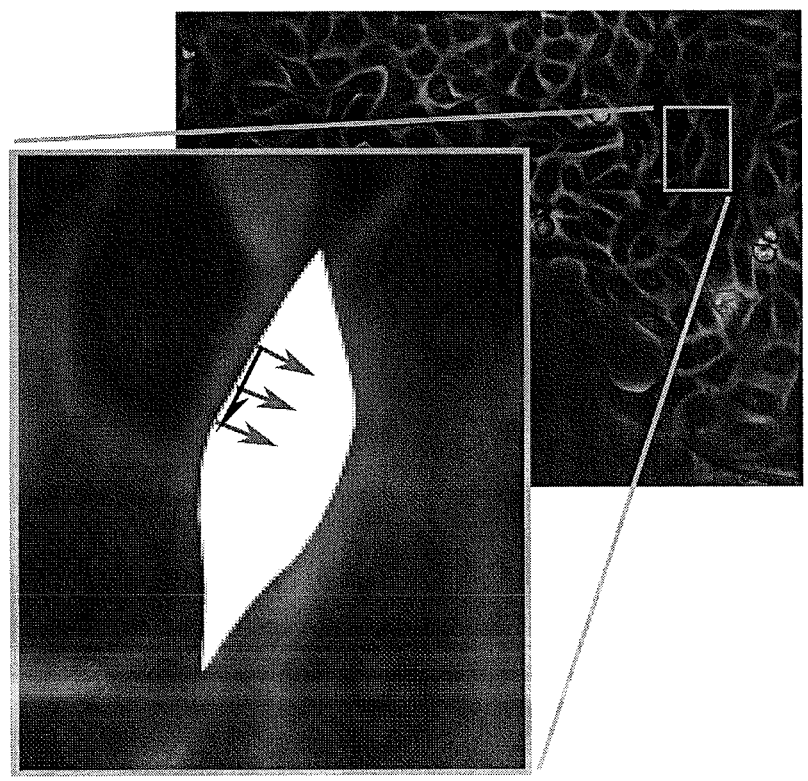
FIG. 1 is a diagram illustrating mechanical forces of migrating cells.

Within a cellular monolayer, physical forces are transmitted between each cell and its substrate, which are called traction forces, and between each cell and its immediate neighbors, which are called the intercellular forces. FIG. 1 is a diagram illustrating mechanical forces of migrating cells. The local intercellular force per unit area of contact defines the local intercellular stress, which comprises two mutually independent components: the normal stress (depicted as arrows acting perpendicular to the local cell-cell junction) and the shear stress (depicted as an arrow acting parallel to the local cell-cell junction). These stresses at the cell-cell junction extend into and become supported by mechanical stresses within the cell body.

As described herein, a cellular monolayer may be a single, closely packed layer of atoms, molecules, or cells. For example, a cellular monolayer may include a planar group of cells that are attached to each other and have structural arrangements ranging from, cells in a single layer with only one cell surrounded by other cells on all sides and all cells adherent to the substrate, to cells forming multiple layers with many cells surrounded by other cells from all sides and the bottom layer adherent to the substrate. Such a monolayer provides, in some embodiments, barrier integrity, as in epithelium or endothelium. In a monolayer, some cells are connected via cell-cell junctions and may be completely surrounded by neighboring cells. In some embodiments, the cellular monolayer may include 2 cells, 5 cells, 10 cells, 100 cells, $1\times10^3$ cells, $1\times10^4$ cells, $1\times10^5$ cells, $1\times10^6$ cells, or any other number of cells.

Figure 2:
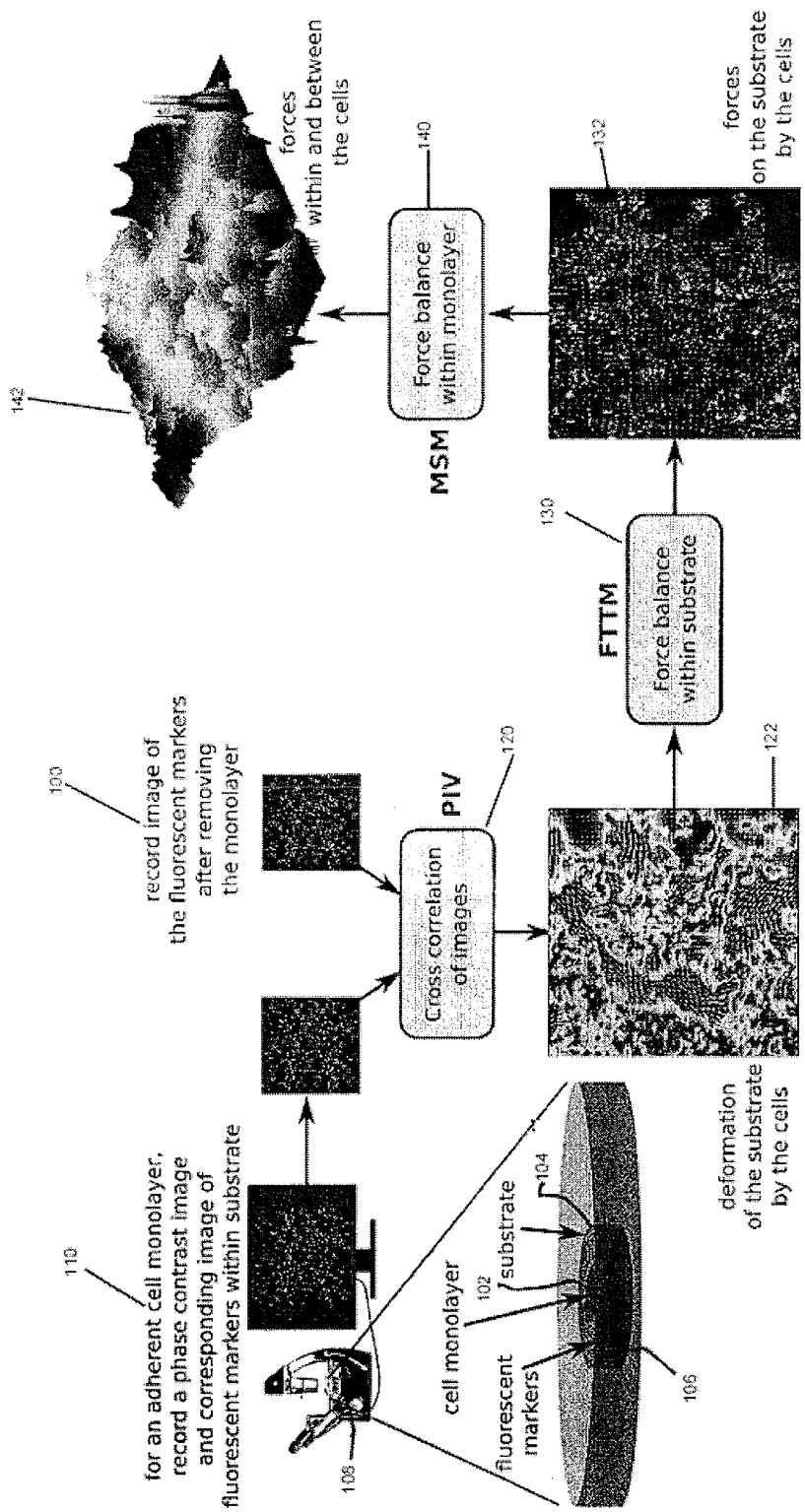
FIG. 2 is a diagram illustrating an example procedure to determine intercellular forces.

With reference to FIG. 2, a diagram illustrating an example procedure 100 to determine internal forces within and between cells of a monolayer (i.e., the intercellular forces) is shown. To determine the intercellular forces, an adherent cell monolayer 102 is placed on a substrate 104 that is embedded with markers 106, such as fluorescence markers. A microscope 108 and an image acquisition device (e.g., a camera, such as a CCD camera) are used to record/capture 110 one or more images and a corresponding image of any marker of gel deformation, in this case the fluorescence markers, in the substrate. The apparatus, including the monolayer placed on the substrate, the microscope and the image capture device are thus used to record cell generated displacements of the gel markers 106 (e.g., fluorescence markers). The displacement of the markers results from two principal components: a) the traction force exerted by the cellular monolayer 102 on the substrate, which causes deformations on the surface of the substrate to form, and b) drift of surface markers (e.g., fluorescence markers) that occurs to drift of the microscope stage. Thus, if the drift of the markers can be determined and accounted for, displacement of the markers resulting from the monolayer's traction forces can be determined, from which the traction forces exerted by the cellular monolayer can be determined. In some embodiments, a suitable substrate to use for the purpose of determining traction forces exerted by the monolayer on the substrate (and thus, intercellular forces) may be a collagen-coated polyacrylamide gel substrate to which the cellular monolayer can adhere.

As noted, traction forces may be determined from substrate (e.g., gel-based substrate) deformations. Deformations may be quantified from images of embedded markers (fluorescent markers) after correcting for microscope stage drift. An example procedure to correct stage drift is implemented by acquiring a phase contrast image of cells and a fluorescent image of markers embedded near the surface of the gel, and then acquiring subsequent image pairs at 5 minute intervals for a period of, for example, 3-4 hours. To account and correct for stage drift, in the subsequently acquired fluorescent images, matched embedded markers in an unstrained region of the gel (e.g., an uncovered area/region of the substrate on which no part of the cellular monolayer is placed) are observed and compared to the same markers from the first fluorescent image. Thus, displacement of fluorescence markers in the unstrained region is generally attributable to the drift of those markers, and accordingly, the drift can be determined from measurements of the fluorescence displacement in the unstrained region of the substrate. In some implementations, drift correction is determined using, for example, an image acquisition program developed using MATLAB. Is such implementations, the technique of recording gel deformation provides highly reproducible and precise measurements. In one set of experiments that was conducted to test the efficacy of the drift determination procedure/technique, cells were detached from the gel surface with isotonic 10× trypsin for 1 hour, followed by acquisition of drift corrected reference image of the fluorescent markers. All experiments were conducted in culture environment (37° C., and 5% $CO_2$) on an inverted optical microscope at magnification 7.5× for RPME cells and 10× for other cells.

Accordingly, in some implementations, determining the substrate deformations may include measuring the substrate deformations based on an acquired image pair, with the image pair including one image of surface makers integrated with a surface of the substrate when the cellular monolayer is placed on the substrate, and another image of the surface markers with the monolayer removed from the substrate. Drift of the surface markers can then be determined based on the acquired image pair, and the deformations of the substrate at the surface are determined based on data of the acquired image pair and based on the determined drift by, for example, applying a numerical technique (e.g., applying a cross-correlation numerical technique) to the drift-corrected image pair to obtain the deformations of the substrate at the surface. In some embodiments, determining the drift includes performing an a priori drift-correction technique based on fixed markers that are not displaced by deformations of the substrate due to the cellular monolayer. Such a technique may use fixed markers in the first image to recover its x-, y-, and z-focus, and use this focus to acquire the second image constituting an image pair representing substrate deformation. An example of the fixed marker includes surface markers from the region that is not covered by the cellular monolayer. A posteriori drift-correction technique that uses images of the fixed markers corresponding to the image pair to compute the drift numerically, with techniques like cross-correlation, and use this computed drift to correct the image pair subsequent to their acquisition.

In some embodiments, a drift correction procedure may also include computing a parameter to quantify alignment of the fixed markers to thus control the adjustment of x-, y-, and z-focus for acquiring drift-corrected second image of the image pair that represents deformation of the substrate. An example of such a parameter to quantify alignment of two images of the fixed markers is root mean square of the difference in intensities of corresponding pixels from the two images.

Operations performed in the course of determining substrate deformations are also depicted in FIG. 2, where, as shown, the acquired images of the sample including the cell monolayer placed on the substrate 104 that includes markers, and of the markers on the substrate after the cell monolayer has been removed, are cross-correlated (at 120 in FIG. 2)

As further shown in FIG. 2, to perform cross-correlation of acquired images, the cellular velocity field within the monolayer is measured by, for example, a particle imaging velocimetry (PIV) procedure (as depicted at 120 of FIG. 2). Specifically, an image from sequence of phase contrast images recorded at an interval $\Delta t$ is compared with the succeeding image. Window pairs, one to each image, can be examined for cross correlation as a function of shifting window position. In some embodiments, the shift of one window relative to the reference (window from image at earlier time) that maximizes the cross correlation function is taken as the displacement of the center of that window. Together with $\Delta t$, this determines the velocity of the central point of the reference window. This procedure is then repeated across the entire field, and a velocity map is constructed at each grid point in the pixelated plane. There is sufficient phase contrast between the cell interiors and the cell-cell boundary junctions such that this procedure may be considered to be robust within the sheet. Based on the measured cellular velocity, an image(s) (such as the image 122 of FIG. 2) with a representation of deformation of the substrate by the cell monolayer is generated.

A traction microscopy procedure, such as, for example, a Fourier-Transform Traction Microscopy (FTTM) procedure, is applied to the data representative of deformations in the substrate to generate traction mapping on the substrate (at 130 of FIG. 2). That is, the traction forces $T_i$ exerted by the cellular monolayer on the substrate, and thus also the forces exerted by the substrate on the cellular monolayer are determined. The FTTM procedure used may be similar to the procedure described in, for example, Trepat, X. et al., "Physical forces during collective cell migration," *Nature Physics* 5, 426-430 (2009), the content of which is hereby incorporated by reference in its entirety. A representation of the data generated through application of an FTTM procedure is provided as an image 132.

Having obtained the traction forces, forces within and between the cells of the monolayer (e.g., intercellular) may be determined based on the determined traction forces by performing a monolayer stress microscopy (MSM) procedure (at 140) such as the MSM procedures described herein. Thus, a two-dimensional balance of forces, as required by Newton's laws, is performed to obtain the distribution of the mechanical line forces everywhere within the cell sheet. For convenience, these measured line forces (in units of force per unit length) are converted to stresses (force per unit area) using the average monolayer height, h (as shown in FIG. 6(a), more particularly discussed below). Gradients of these line forces and stresses within the cell sheet are attributable to the pileup of traction forces applied on the underside of the cells. At each point within the sheet the local coordinate system (as shown in FIG. 6(c)) can be rotated in the cell plane in order to find those special orientations along which the local normal stress is maximal and minimal, respectively, thus defining the two principal stress components ($\sigma_{max}$ and $\sigma_{min}$) and the two corresponding, mutually perpendicular, principal orientations (as shown in FIG. 6(d)). As such, the associated MSM result enables displays of individual components of the in-plane stress tensor. A representation of the resultant forces within and between the cells of the monolayer is shown as image 142 of FIG. 2.

Figure 6:
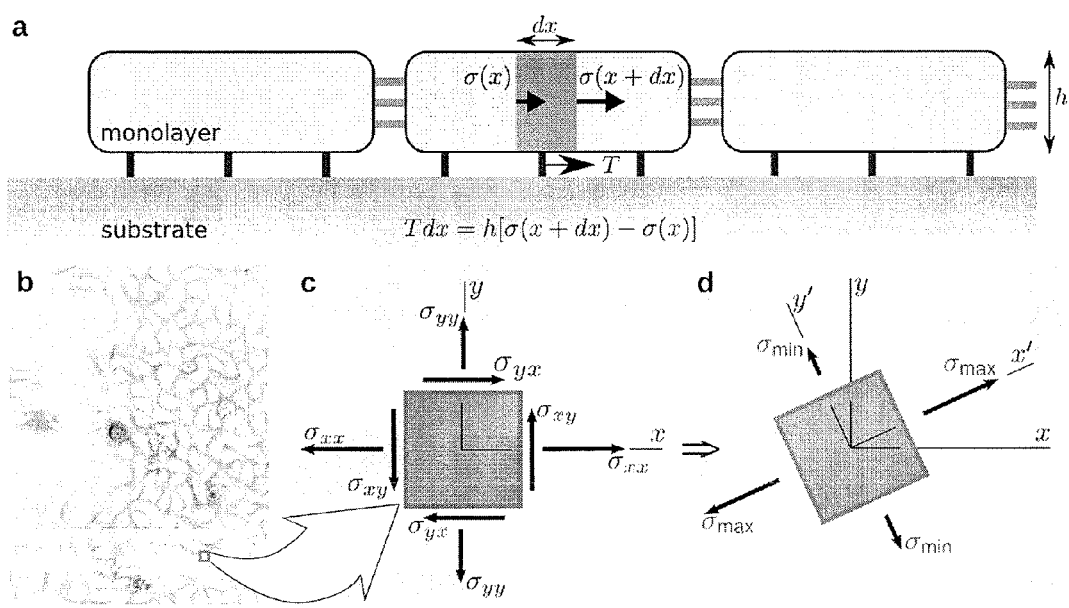
FIG. 6 includes views and diagrams illustrating monolayer stress microscopy.

FIG. 6 is a simplified representation of the physical relationship between cell-substrate tractions, T and intercellular stresses, $\sigma$. As noted, intercellular stresses arise from the accumulation of unbalanced cell-substrate tractions. At any point within the monolayer (an example of which is shown in FIG. 6(b), the intercellular stresses, defined in laboratory frame (x, y), (as depicted, for example, in FIG. 6(c)), have shear ($\sigma_{xy}$, and $\sigma_{yx}$) and normal ($\sigma_{xx}$, and $\sigma_{yy}$) components. This frame may be rotated locally to obtain the principal frame (x', y'), (as shown, for example in FIG. 6(d)), where shear stresses vanish and the resulting normal stresses are called principal stresses ($\sigma_{max}$ and $\sigma_{min}$). The corresponding axes are called maximum, aligned with x', and minimum, aligned with y', principal orientations.

The intercellular stress is a local outcome of the overall balance of cell-substrate tractions across the entire monolayer as required by Newton's laws. Traction forces exerted locally by each cell on the substrate are balanced at distances significantly larger than the size of the cell. Local variations in monolayer height can induce moments and out-of-plane stresses in principle, but the lateral extent of the monolayer in question here is at least three orders of magnitude greater than the thickness, and that thickness is approximately uniform (as depicted, for example, in FIG. 14). Such a system therefore lends itself naturally to a formal two-dimensional balance of line tensions (force per unit length) in a system of zero thickness, and makes recovery of intercellular line tensions rigorous.

Figure 14:
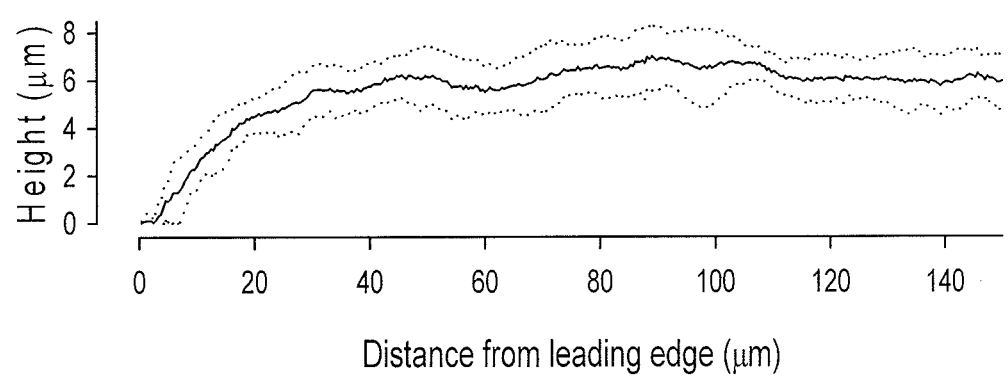
FIG. 14 is a graph showing height of an MDCK monolayer expressing GFP-actin.

FIG. 14 is a plot illustrating height of an MDCK monolayer expressing GFP-actin. Cell height is measured using confocal microscopy (60×). The coefficient of variation is close to 20%. The solid line is the mean height and the dotted lines are mean±standard deviation.

As a matter of computational convenience, in some embodiments, the two-dimensional force balance within the monolayer is computed by representing the cellular monolayer as a thin elastic sheet. This approach is generally permissible because, if the traction distribution is known, then the force balance itself does not depend upon cell material properties. Line tensions (in units of force per unit length) and the more familiar units of stress (force per unit area) are related through a uniform monolayer height, h (as illustrated in FIG. 14), but the underlying force balance itself, being two-dimensional, does not depend upon the assumption of uniform cell height.

Accordingly, the internal stress tensor $\sigma_{ij}(x, y)$ is treated as plane stress in the x, y plane, where i and j run over the coordinates x, y; all stress components associated with the z direction vanish. The measured local tractions $T_i(x, y)$ are the components of the shear stresses exerted by the cells on the substrate, and hence by Newton's third law, the forces exerted by the substrate on the monolayer are simply the negative of these tractions. Because at any instant there is no net force on the monolayer as a whole, these tractions substantially balance the internal stresses generated within the monolayer. This balance of forces may be represented by the equations of mechanical equilibrium, namely, $$\sigma_{ij,j} = T_i \quad \text{(Eq. 1)}$$

where Einstein convention of summation over repeated indices is used and $(\ )_{,j}$ denotes $\partial/\partial x_j$. As noted from the form of Eq. 1, the source term on the right hand side can be thought of equivalently as a body force, although one that is non-uniform and time-varying. The internal stresses, $\sigma_{ij}$, are those required to balance the measured traction forces irrespective of whether monolayer material is active or passive, elastic or visco-elastic, linear or nonlinear. An assumption used is that the monolayer can be treated as a continuum.

Figure 4:
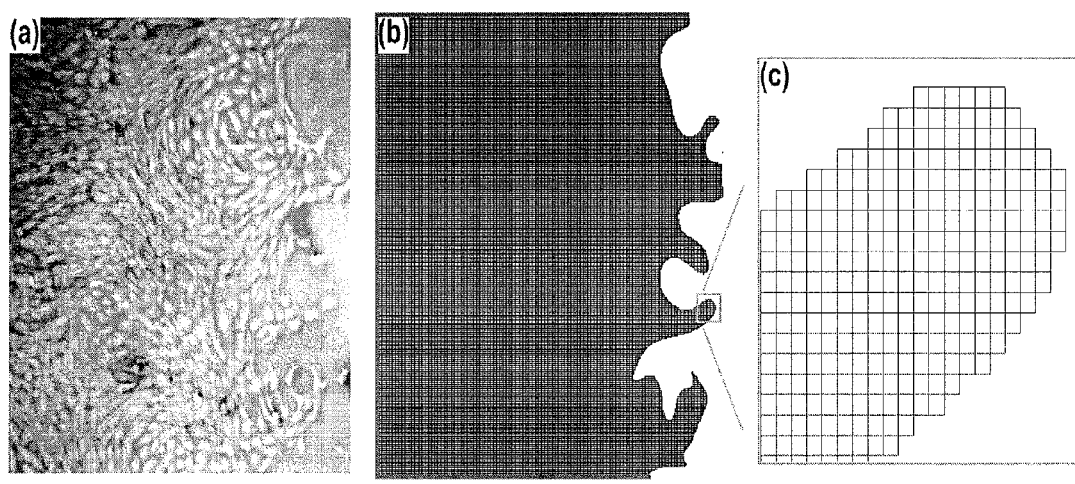
FIGS. 4A-C are diagrams and views of an example finite element representation of a monolayer.

Equation 1 provided above describes an elliptical boundary value problem. Boundary conditions on the free edge of the monolayer were taken to be homogeneous in stress, $\sigma_{ij}n_j=0$. Boundary conditions at the edges of the field of view were taken as zero normal displacement, $u_jn_j=0$, where $n_j$ denotes the components of the vector normal to the boundary. Imposition of this zero normal displacement condition is physically equivalent to continuing the monolayer outside the field of view as a mirror image, but this continuation introduces artifactual reaction forces along the boundary. Depending upon their spatial distribution, the stresses due to these reaction forces decay as 1/r, or faster, but far from the edges the local stress field is dominated by the source term—the traction forces, $T_i$. As such, regions in which the boundary effects contribute appreciably to the result can be cropped out (see FIG. 4, further described below). To quantify associated errors, in some embodiments, scatter plots of average normal stresses within the inner region are computed from the maximum (actual) field of view edges against those calculated from successively smaller (cropped) fields of view. Up to a cropping distance of 60 µm from the maximum field of view, the average normal stresses within the inner region were found to be strongly correlated ($r^2 > 0.98$, $0 < \text{intercept} < -20$ Pa, and $1 < \text{slope} < 0.95$), thus establishing insensitivity of stresses in the inner region to the placement of the boundary.

Thus, in some implementations, determining the internal stresses that act to balance the determined traction forces over the at least part of the monolayer may include determining the internal stresses resulting from imposing mechanical equilibrium of the forces according to $\sigma_{ij,i}=T_i$, where $\sigma_{ij}$ represents internal stress at a point i within the cellular monolayer, and at the same position, $T_i$ represents a traction force exerted by the substrate on the cells at the point i. Determining the internal stresses resulting from imposing mechanical equilibrium of the forces according to $\sigma_{ij,i}=T_i$ may include performing one or more numerical techniques to solve equations of the mechanical equilibrium over a mathematical representation of the at least part of the cellular monolayer subjected to the traction forces using boundary conditions set along one or more of, for example, the optical field of view and/or free edges of the monolayer. For example, in some implementation, a numerical scheme, such as Fast Fourier Transform (FFT) may be used to solve equations of mechanical equilibrium over the at least part of the substrate subjected to the displacements on the top surface arising from gel deformation due to the adherent cells. Conditions at other boundaries represent physical state of the substrate. For example, if the substrate is glued to hard surface at the bottom then that surface is considered to have zero displacements.

Additionally, determination of the internal stresses may further include setting boundary conditions at a boundary determined based on an optical field of view (i.e., an optical view of an observed section of the monolayer), determining errors associated with the setting of the boundary conditions, and identifying an inner region in which the determined errors are negligibly, or acceptably, small. For example, in some embodiments, the determined errors may be deemed to be acceptably small when the errors are smaller than a pre-determined error threshold (that may be set according to the desired acceptable error). For example, the pre-determined error threshold may be set to 10%, but may be set to higher or lower values). The setting of boundary conditions may include setting the boundary conditions along the optical field of view when a region within the boundary does not include a free edge of the monolayer, and setting the boundary conditions along an edge defined by sides of a group of cells that do not abut sides of another group cells from the monolayer when the optical field of view includes free edges of the monolayer. In some embodiments, the boundary conditions at the boundary determined based on the optical field of view may be set to have a zero normal displacement.

In some implementations, eigenvalue decomposition of the stress tensor defines the principal stresses ($\sigma_{max}$ and $\sigma_{min}$) and the corresponding mutually perpendicular eigenvectors define the local orientation of these stresses. By definition, each of these eigenvectors also defines the orientation of zero shear stress. The scalar tension within the sheet which is local average normal stress, defined as $(\sigma_{max}+\sigma_{min})/2$, may be computed.

Solving the equilibrium equations is equivalent to solving the boundary value problem of minimization of total potential energy per unit thickness of the monolayer defined by $$\Pi = \int\int_R \left(\frac{1}{2}\sigma_{ij}\varepsilon_{ij} - u_j T_j\right)dxdy,$$

where $\epsilon_{ij}$ is the planar strain tensor, and R is the bounded domain, subjected to the boundary conditions described above. Thus, this function with respect to displacements $u_j(x, y)$ can be minimized such that conditions at the domain boundaries are satisfied. From these displacements, which are compatible, both strains and stresses in the monolayer may be computed.

As noted above, the specific material properties of the monolayer have no effect on the recovered distribution of intercellular forces. Without loss of generality, therefore, the monolayer may be treated as an isotropic homogeneous elastic sheet with Young's modulus of 10 kPa, Poisson's ratio of 0.5, and height of 5 µm. With reference to FIGS. 4(a)-(c), diagrams of an example finite element representation of a monolayer is shown. In FIG. 4(a), an image of an RPME cell monolayer (890×890 µm$^2$) is shown, where the cell monolayer is bounded by a free edge on one side and edges defined by the field of view on all three sides (effectively cropping out the cellular regions of the monolayer at those three sides). As depicted in FIG. 4(b), the monolayer sheet is uniformly discretized into, for example, four-node square elements such that the FEA grid matches the traction grid recovered from performing a traction microscopy procedure (such as a Fourier Transform Traction Microscopy, or FTTM, procedure). This grid is dense enough so that the internal stresses essentially independent of the size of elements. FIG. 4(c) illustrates a magnified view of a local region in FIG. 4(b) (where each depicted square may have dimensions of 2.61×2.61 µm$^2$).

In implementations based on an FEA-based procedure, a boundary value problem is transformed into a system of linear equations, which are solved for the local displacements using standard Cholesky factorization. From these displacements we calculate stresses through the constitutive equation $\sigma_{ij}=\frac{2}{3}E(\epsilon_{ij}+\epsilon_{kk}\delta_{ij})$ where $\delta_{ij}$ is the Kronecker delta. Explicitly, $\sigma_{xx}$ and $\sigma_{yy}$ are normal stresses along the laboratory x- and y-axes, and $\sigma_{xy}$ ($=\sigma_{yx}$) is the shear stress, also in the laboratory frame. Diagonalizing $\sigma_{ij}$ amounts to a rotation, equivalent to the eigenvalue decomposition noted above, from which the principal stresses are obtained, and in this rotated system the shear stresses are zero. In some embodiments, the FEA-based procedure may be implemented in any number of ways, including using software-based implementations (e.g., implementations using an in-house FORTRAN90 program).

In some embodiments, other procedures (i.e., other than FEA-based procedure) may be used to determine intercellular forces exerted by cells of the cellular monolayer. Examples of such other procedures may include finite difference solutions, analytical solutions, etc.

It is to be noted that anisotropy and heterogeneity of material properties can influence the magnitude of stresses, but contribute only weakly to the recovery of orientation of planes with zero shear stress. This weak dependence was confirmed through the observation that in RPME cells the maximal principal stress orientations which are local axis of highest tension aligns with the cell orientation which, for these spindle-like cells, is largely orientation of actin stress fibers.

Figure 5:
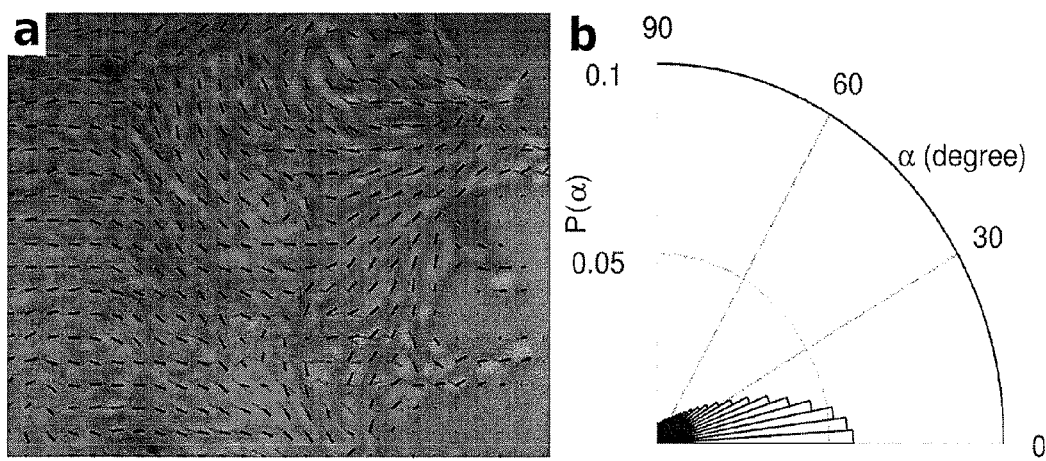
FIG. 5 includes images and diagrams showing cells in RPME monolayers aligning with local orientation of maximum principal stress.

FIGS. 5(a)-(b) are views and diagrams illustrating that in an endothelial monolayer, the long axis of a cell tends to align with the orientation of local maximum principal stress. Particularly, FIG. 5(a) is an image of the RPME cell monolayer in which an image of the orientation of long axis of the cells is overlapped with an image of the orientation of maximum principal stresses. The local cellular orientation is the orientation of major axis of an ellipse that has same second-moments of 20×20 µm$^2$ region of the transmitted light image of the monolayer. In the example implementation described herein, the map of cell orientation was generated using image processing toolbox of MATLAB.

FIG. 5(b) shows the distribution of angle, α, between the cell orientation and maximum principal stress orientation, illustrating that the cell orientation and maximum principal stress orientation tend to align. The distribution is composed of more than 8000 observations.

Figure 3:
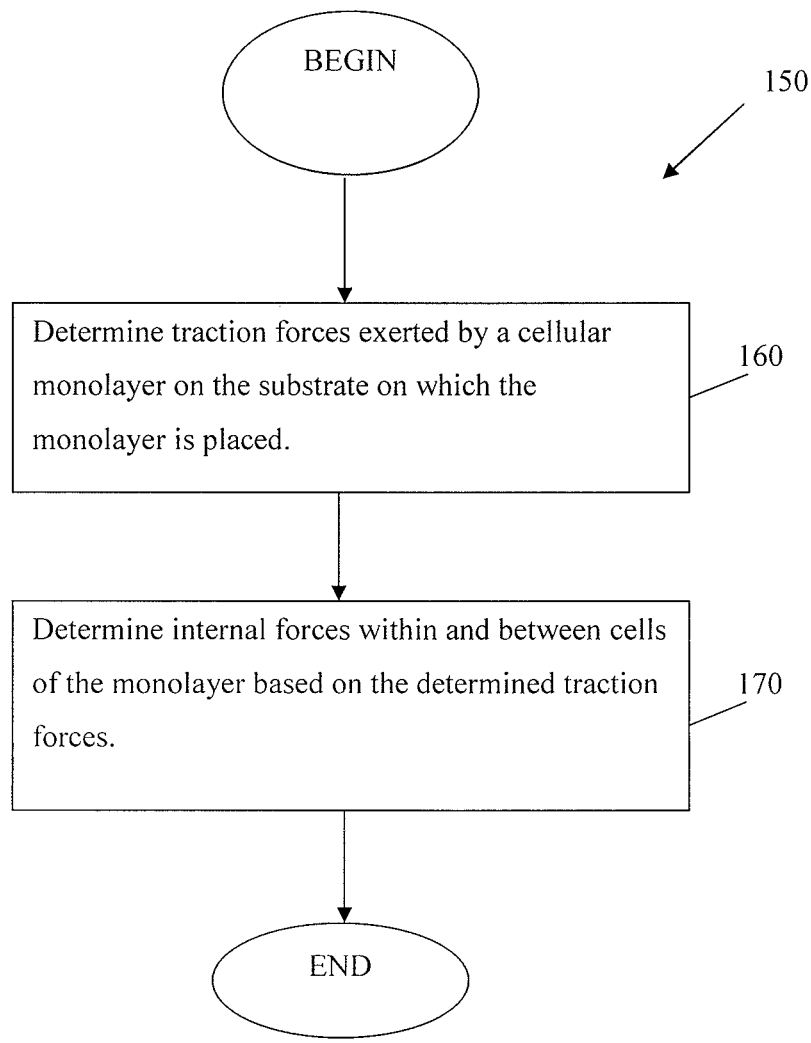
FIG. 3 is a flow chart of an example procedure to determine intercellular forces in a cellular monolayer.

With reference to FIG. 3, a flow chart of an example procedure 150 to determine internal forces in a cell monolayer is shown. The procedure 150 includes determining 160 traction forces exerted by a cellular monolayer on a substrate on which the cellular monolayer is placed/disposed. As described herein, determination of the traction forces may be performed by obtaining a sequence of phase contrast images of locations and displacement of markers (e.g., fluorescence markers) in the substrate as a result of deformations in the substrate (caused by the traction forces exerted by the cellular monolayer), auto-correlating the images (e.g., employing particle imaging velocimetry (PIV) based procedure), and performing a Fourier-Transform Traction Microscopy (FTTM) procedure to obtain a traction map.

Having determined the traction forces exerted by the cellular monolayer on the substrate, the internal forces within and between a cellular monolayer are determined 170 based on the determined traction forces. As described herein, in some embodiments, determination of the intercellular forces may be determined by within and between the cells of the monolayer may be performed by determining the $\sigma_{ij}$ required to balance the measured traction forces. Since at any instant there is no net force on the monolayer as a whole, these tractions must precisely balance the internal stresses generated within the monolayer. As described herein, this balance of forces is represented by the equation of mechanical equilibrium of $\sigma_{ij,j}=T_i$.

As also described herein, in some implementations, determination of the intercellular forces also includes the imposition of boundary condition, and the cropping out of regions in which the boundary effects contribute appreciably and erroneously to the resultant stress forces to be computed. To determine the region(s) that are to be cropped and quantify associated errors, scatter plots are made of average normal stresses within an inner region as calculated from the maximum (actual) field of view edges against those calculated from successively smaller (cropped) fields of view. Thus, in such implementations, cellular stress forces occurring outside a specified boundary are cropped out, an error value representative of a computation error resulting from the cropping out of the cellular stress forces occurring outside the boundary is computed, and an inner region in which the computed error is negligibly or acceptably small (e.g., the error is smaller than a pre-determined error threshold) is determined.

Having described the apparatus and procedures to perform monolayer stress microscopy (MSM) to determine intercellular forces within and between cells of a monolayer based on traction forces exerted by the monolayer on a substrate, a discussion and analysis of results obtained from performance of MSM follows. In the course of investigating intercellular force behavior, several tissue samples were used, including the cell cultures listed and described in FIG. 15.

Figure 7:
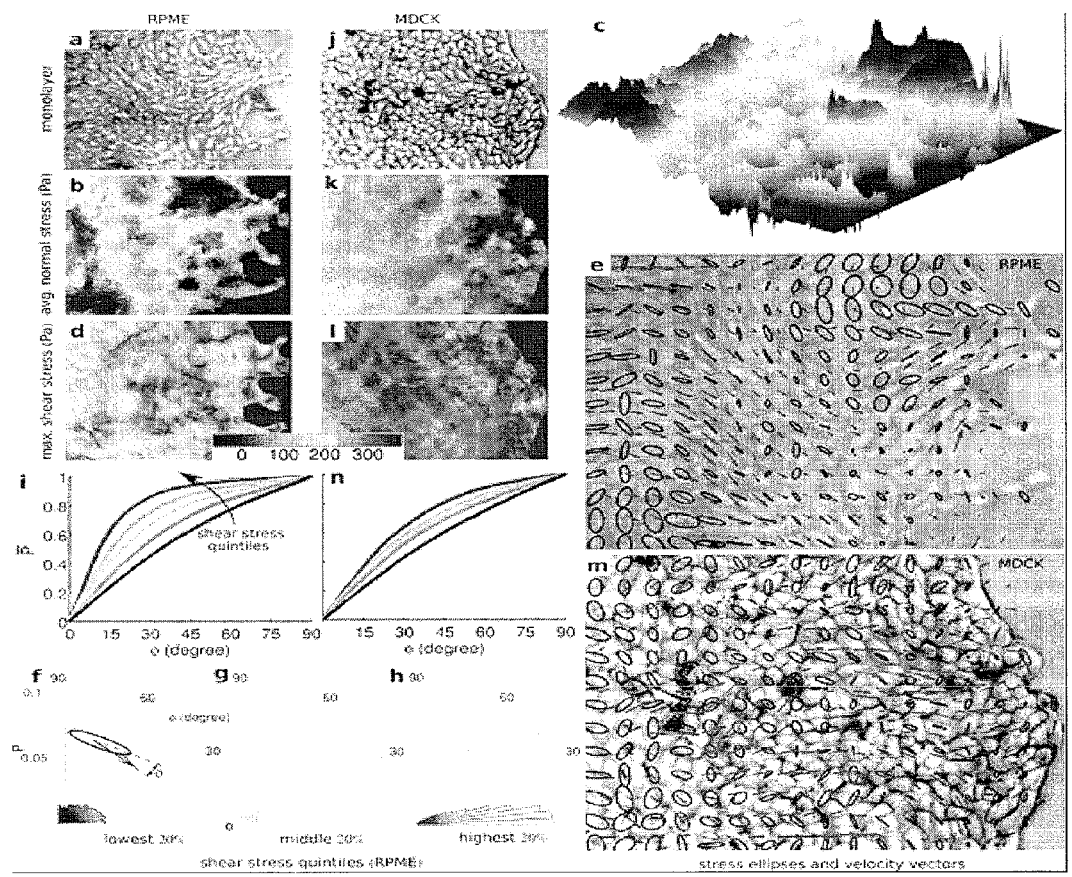
FIG. 7 includes views, images, and diagrams of intercellular stress maps obtained from rat pulmonary microvascular endothelial (RPME) cell monolayer.

With reference to FIG. 7, views and images of intercellular stress maps obtained from rat pulmonary microvascular endothelial (RPME) cell monolayer are shown. Consider first the average local normal stress, simply defined as $\bar{\sigma}=(\sigma_{max}+\sigma_{min})/2$, and its spatial heterogeneity. A traditional image of an advancing monolayer of the (RPME) cells, as illustrated in FIG. 7(a) is unremarkable. The underlying distribution of local normal stress, by contrast, is severely heterogeneous; normal stresses are mostly positive (tensile) with values exceeding 300 Pa in regions spanning tens of cells. These regions of predominantly tensile stresses alternate with regions of weakly negative (compressive) stresses (as illustrated in FIG. 7(b)). These fluctuations occur steadily over distances spanning multiple cell widths and define a stress landscape that is rugged (as shown in FIGS. 7(b) and 7(k)), meaning that the spatial fluctuations over these relatively short distances are comparable in magnitude to the spatial mean values.

Consider next the distribution of the intercellular shear stress which is not to be confused with any additional shear stress that might be imposed by flow over the monolayer surface, which in this case is zero (0) everywhere. As in the case of the normal stress, the shear stress at a point within a material varies with orientation and attains its maximal value, $\mu=(\sigma_{max}-\sigma_{min})/2$, at 45° from the principal orientations. The local maximal shear stress was systematically smaller than the local normal stress, but was also characterized by a rugged landscape (as illustrated in FIG. 7(c)). As the monolayer advances, these respective stress landscapes evolve continuously in time. Finally, dependence of local stresses upon orientation signifies stress anisotropy. To visualize this anisotropy, ellipses whose major axes correspond to the local $\sigma_{max}$ and whose minor axes correspond to the local $\sigma_{min}$, each aligned with corresponding principal orientations, were plotted (see FIG. 7(e)). Where $\sigma_{max}=\sigma_{min}$ the stress field is isotropic, the ellipse becomes a circle, μ is zero, and there exists no preferred stress orientation. But where $\sigma_{max}\gg\sigma_{min}$ the local stress field is highly anisotropic, the ellipse becomes spindle-like, μ is nonzero, and there exists a strongly preferred and well-defined stress orientation. From region-to-region, it was found that ellipse size, ellipse shape, and ellipse orientation varied extensively, but with strong local correlations.

Figure 8:
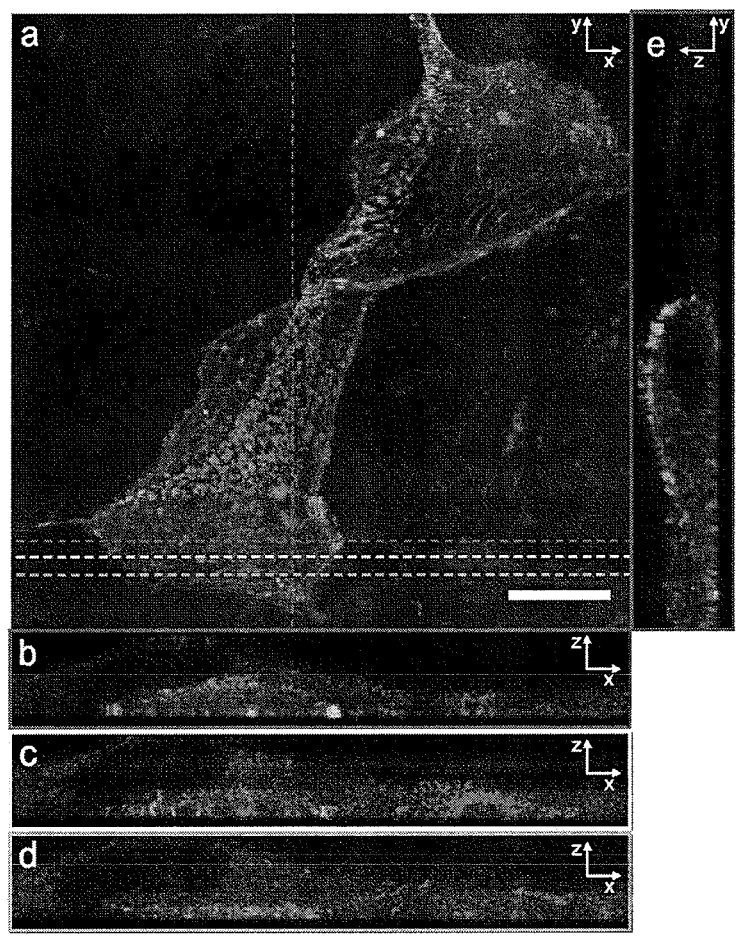
FIG. 8 includes images of observation of lamellipodial protrusion by the submarginal cells within an expanding MDCK cell monolayer.

As cells extend cryptic lamellipodia and advance within the monolayer, stresses at every point and at every instant of time have to be in mechanical balance. Particularly, it has been reported that cells in a wound or scratch assay located many rows behind the leading edge protrude underneath their neighbors. These protrusions are called "cryptic lamellidopia." To test whether submarginal cells within an expanding MDCK monolayer also extend cryptic lamellipodia, an epithelial colony containing MDCK cells stably expressing either actin-GFP or α-actinin-RFP was seeded. Using confocal microscopy during expansion of the colony, abundant cryptic lamellipodia at least 20 rows behind the leading edge was observed (as illustrated in FIG. 8). Therefore, wounding is not required for the existence of cryptic lamellipodia in submarginal cells.

To determine the extent to which intercellular stresses provide meaningful biologically and useful predictivity, two pieces of experimental evidence should be considered. First, the coincidence between orientation of the cell body versus orientation of the maximal principal stress is striking (see FIG. 7(e)). Further, because the maximal principal orientation corresponds to the local axis of highest normal stresses and zero shear stress, this result suggests that the cell-cell junction, as well as the cell body, support high normal stresses, which are overwhelmingly tensile, but only minimal shear stresses. One would predict, therefore, that major organized actin structures that span the cell, as would be imaged at low resolution, might align with maximal principal orientations, and for the spindle-like RPME cells this is in fact seen to be the case. Second, cells not only align with the maximal principal orientation, but also migrate along that orientation. Appreciable portions of the stress field are approximately isotropic, however, and therefore the local orientation of cell motion would not be expected to correlate with a stress field possessing no preferred orientation.

These observations lead to the following prediction: regions of higher stress anisotropy will exhibit stronger alignment between the direction of local maximal principal stress and that of local cellular migration velocity. To test this prediction, the following reasoning has been used. Since the maximum local shear stress is given by $\mu=(\sigma_{max}-\sigma_{min})/2$, $\mu$ was taken as a direct and quantitative index of stress anisotropy. This stress anisotropy was then rank-ordered by quintiles. For each point within the cellular monolayer falling within any given quintile, the alignment angle $\phi$ between the orientation of the local maximal principal stress and the orientation of the local cellular migration velocity vector was measured (as illustrated, for example, inset, FIG. 7(f)). The greater was the local shear stress, the narrower was the distribution of $\phi$ (as shown in FIGS. 7(f), (g), and (h)).

Figure 9:
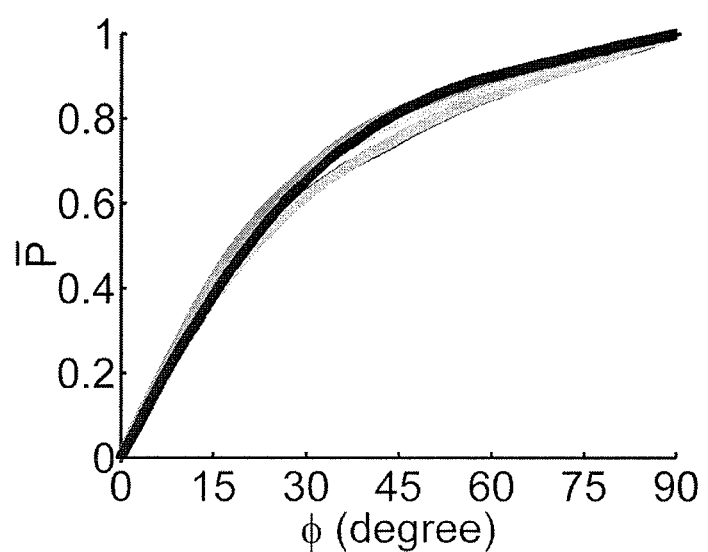
FIG. 9 is a graph of cumulative probability distribution of an alignment angle, $\phi$, plotted as a function of quintiles of local average normal stress.

The cumulative probability distribution function, $\overline{P}(\phi)$, was then determined in accordance with the reasoning that if there were perfect alignment between the orientation of local cellular migration velocity and that of local maximal principal stress, then all angles would be 0° and the cumulative probability distribution would be a step function from probability 0 to probability 1 occurring at 0°. On the other hand, if there were no alignment then all angles between 0° and 90° would be equally likely, and the cumulative probability function would be a straight line from probability 0 at 0° to probability 1 at 90°. In the regions with lowest stress anisotropy, the angular distribution was broad but not uniform. In regions with highest stress anisotropy, the angular distribution was quite narrow; the orientation of cellular velocity and the orientation of maximal principal stress were coupled strongly, but were unrelated to the magnitude of local average stress (as also illustrated in FIG. 9). The stronger the stress anisotropy was, the greater was the overall degree of alignment.

FIG. 9 is a plot illustrating that the cumulative probability distribution is independent of magnitude of local average normal stress. For RPME cell monolayers, cumulative probability distribution of the alignment angle, $\phi$, is plotted as a function of quintiles of local average normal stress. The magnitude of local average normal stress is unrelated to the shape of $\overline{P}(\phi)$. Each curve has more than 8,000 observations.

To assess the generality of this finding, monolayers comprising Madin-Darby canine kidney (MDCK) cells (as shown in FIG. 7(j)) were then examined. These cells are of particular interest because they are epithelial, not endothelial, and because they are rounded in the plane, not spindle-shaped as are RPME cells. Despite these differences in cell type and cell morphology, the stresses were dramatically heterogeneous (as illustrated in FIGS. 7(k), and (l)) and the local orientation of cellular migration was also found to follow the local orientation of maximal principal stress (as shown in FIGS. 7(m), and (n)). Local cell motions tended to follow local principal stress orientations even when local cell geometry displayed no preferred orientation.

To assess further the generality of this finding, the behavior of monolayers of well-established breast-cancer model systems were examiner. These cells included the MCF10A cells (control or vector) (shown in FIG. 10(a)), MCF10A cells overexpressing ErbB2/HER-2/neu (shown in FIG. 10(b)), and MCF10A cells overexpressing 14-3-3ζ (shown in FIG. 10(c)). These cell lines were chosen because each line exhibits pronounced morphological differences as well as diverse levels of transforming potential, expression of cell-cell junction proteins, and cell proliferation. Much as in the case of endothelial cells and control epithelial cells, ErbB2 cells moved in alignment with the direction of maximum principal stress (as illustrated in FIG. 10(m)). By contrast 14-3-3ζ cells, which have decreased expression of cell-cell junctional markers, were seen to move nearly independently of the orientation of the maximum principal stress (as shown in FIG. 10(m)).

Figure 10:
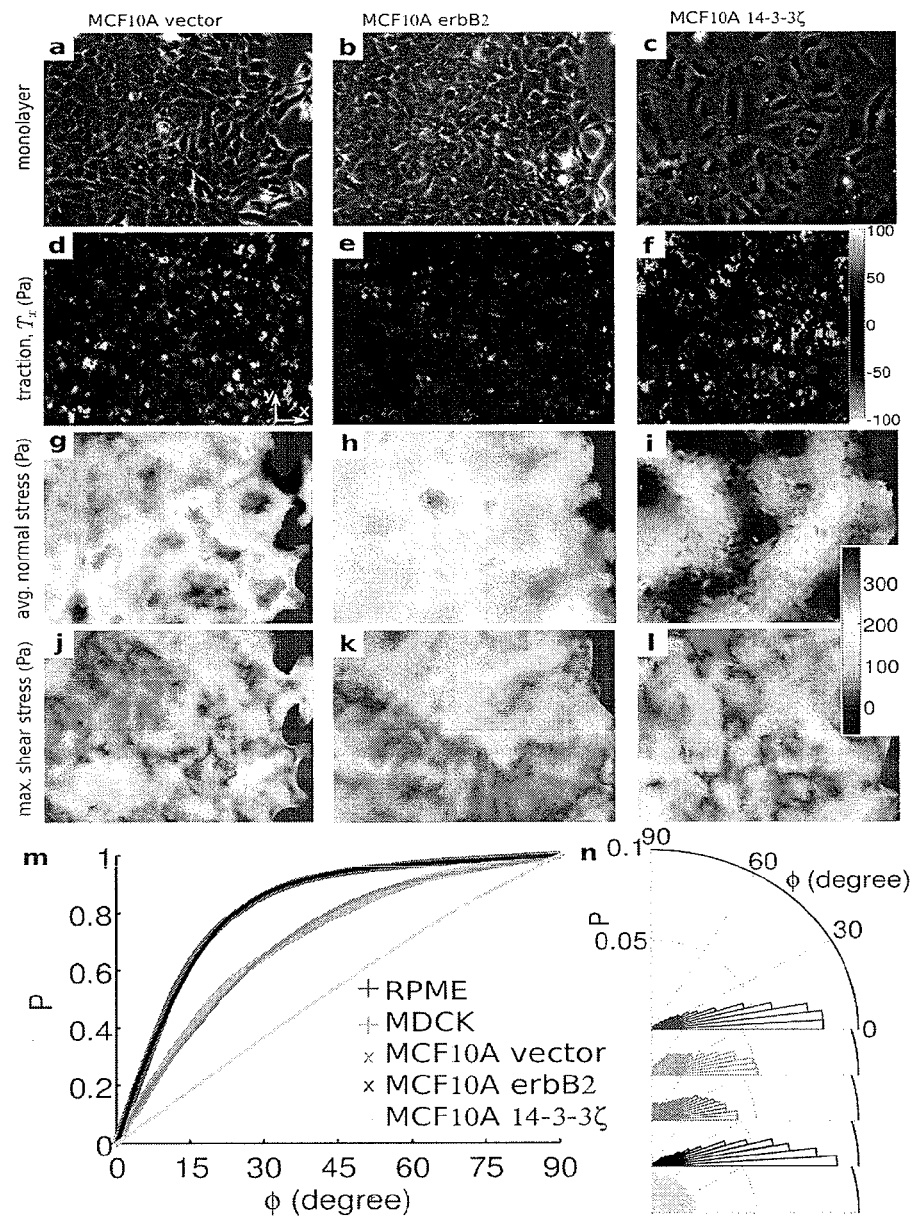
FIG. 10 includes stress maps and migration in monolayers of breast-cancer model systems.

FIG. 10 is a series of plots illustrating stress maps and migration in monolayers of breast-cancer model systems. Phase contrast image of nontransformed human mammary epithelial cell line, MCF10A, control or vector (a), cells overexpressing ErbB2 (b), and 14-3-3ζ (c). Maps of cell-substrate tractions, $T_x$, (d, e, f), normal stress (g, h, i), and maximum shear stress (j, k, l) corresponding to each of these three mammary epithelial cell lines. (m) Cumulative probability distribution of $\phi$ for the regions corresponding to highest quintile of the shear stress for five different cell sheets. (t) Distributions corresponding to the curves in (m). Vertical size of the images of monolayer: 410 µm. Each curve in (m) has more than 8,000 observations.

To further assess the importance of cell-cell adhesion, cell-cell contacts of MCF10A vector cells were weakened by calcium chelation (shown in FIGS. 11(g), and (i)). As expected, alignment between orientations of local stress and orientation of local cellular motions was lessened (shown in FIG. 11(s)), but was restored upon returning to normal growth medium (FIG. 11(i), (s)). This reversibility was blocked in the presence of E-cadherin antibodies, however (as shown in FIGS. 11(r), and (s)). Together, these observations establish that transmission of mechanical stresses from cell-to-cell across many cells is necessary for plithotaxis, i.e., for each individual cell to follow the local orientation of the maximal principal stress.

Figure 11:
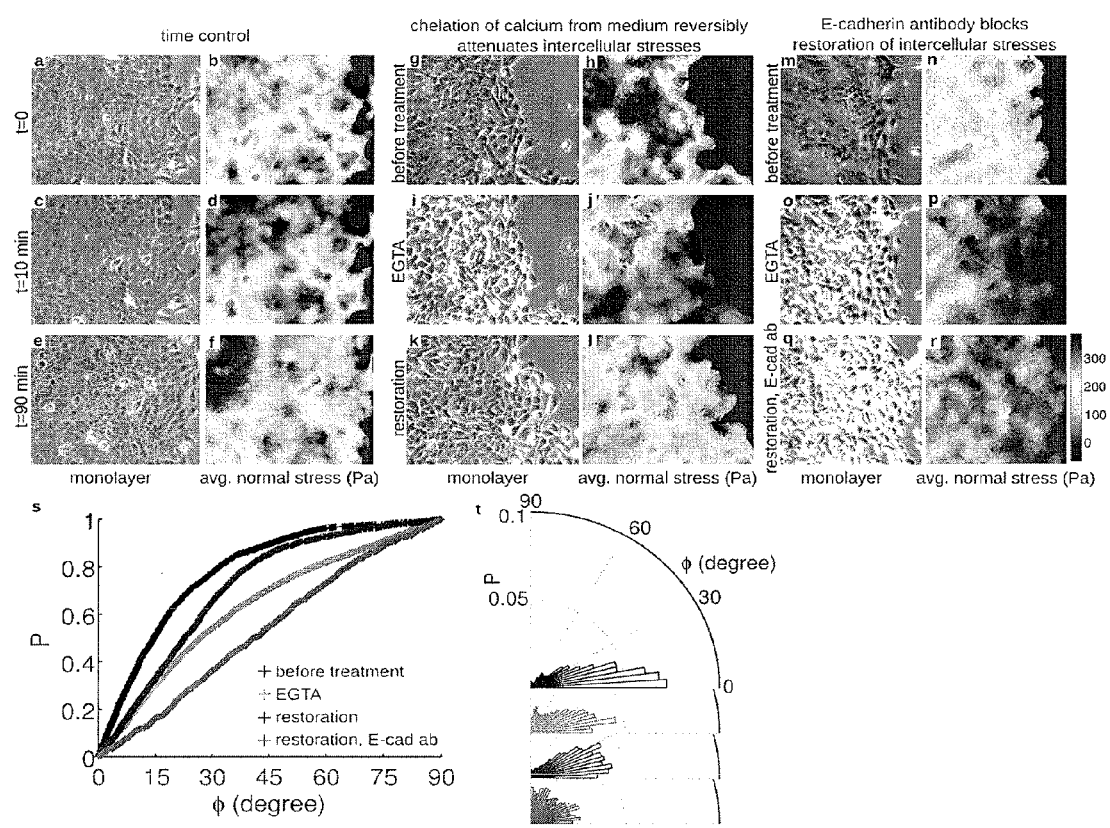
FIG. 11 includes stress maps and graphs of cumulative probability distribution for human mammary epithelial cells (MCF10A) showing effect of adherence junctions formed between the cells.

FIG. 11 is a series of plots illustrating how local cell guidance requires force transmission from cell-to-cell. Time-controls of intercellular stress maps of MCF10A-vector cell monolayers (a-f). The stress patterns do not change appreciably over a period of 80 minutes. After 10 minutes in presence of the calcium chelator EGTA (4 mM), however, cells lose contacts with their neighbors (g, i and m, o). These changes lead to attenuation of intercellular average normal stress (h, j and n, p). After returning to normal growth medium for 80 minutes, the stresses and the cell-cell contacts are largely restored (k, l), but if the growth medium is supplemented with E-cadherin antibody (7 µg/ml) recovery of stresses and cell-cell contact is blocked (q, r). EGTA treatment widens the distribution of angle ($\phi$) between local cellular velocity and local maximum principal orientation corresponding to highest of the maximum shear stress quintiles (s, t). The distribution of $\phi$ is narrowed if calcium is restored (s and t), but widened further if the restoration medium is supplemented with E-cadherin antibody (s and t). Together, these data show that local cell guidance along the orientation of maximal principal stress (plithotaxis) requires force transmission across cell-cell junctions. These preferred orientations correspond to those engendering minimal intercellular shear stresses. Increased intensity at cell boundaries (panels i, o, and q) reveals a disruption of cell-cell junctions. Vertical size of the images of monlayer: 410 µm. Each data set in (s and t) has more than 1,500 observations.

For collective migration to be coordinated across many cells, intercellular stresses might be expected to be cooperative over comparable distances; cooperativity of cell motions have been recently established, but cooperativity of cellular stresses have not. To quantify the spatial extent of any such stress cooperativity, the spatial autocorrelation function of the average normal stress is examined. Specifically:

$$C(R) = \frac{1}{N \operatorname{var}(\overline{\sigma})^2} \sum_{i,j=1}^{N} \sum_{|\vec{r}_i - \vec{r}_j| = R} \delta\overline{\sigma}_i \cdot \delta\overline{\sigma}_j$$

where $\delta\overline{\sigma}_i$ is the local departure of the average normal stress at position $\vec{r}_i$ from its spatial mean $\langle\overline{\sigma}_i\rangle$, $\operatorname{var}(\overline{\sigma})$ is the variance of those departures, and the notation $|\vec{r}_i - \vec{r}_j| = R$ means equality within a uniform bin width of 5 microns. Confining attention to regions many cell lengths from the leading edge of an MDCK monolayer (as shown in FIG. 12(a)), fluctuations in normal stress (FIG. 12(c)) were found to be correlated over a length scale of approximately 10-15 cell diameters (FIG. 12(e)). Cooperativity of normal stresses over 10-15 cell diameters might be attributable to alignment of principal stresses end-to-end, as in a tug-of war, or side-by-side, as police who lock arms during crowd control. To assess whether normal stresses are aligned according to either of these configurations, the maximum principal stress was decomposed into end-to-end and side-by-side contributions, $$C_{end}(R) = \frac{1}{N\|F\|^2} \sum_{i,j=1}^{N} \sum_{|\vec{r}_i - \vec{r}_j| = R} \vec{F}_i \cdot \vec{F}_j \cos^2\theta_{ij}$$

$$C_{side}(R) = \frac{1}{N\|F\|^2} \sum_{i,j=1}^{N} \sum_{|\vec{r}_i - \vec{r}_j| = R} \vec{F}_i \cdot \vec{F}_j \sin^2\theta_{ij}$$

where $\|\ldots\|$ denotes $L^2$ norm, $F_i$ is the local maximal principal stress considered as a vector quantity (such that the angle between the maximal and minimal principle stress orientations is taken modulo $\pi$) and $\theta_{ij}$ is the angle between adjacent vector pairs. The two components were found to contribute almost equally to force cooperativity, thus indicating the coexistence of both end-to-end and side-by-side force correlations (FIG. 12(f)). Simply put, in order to move, cooperatively neighboring cells join forces.

Cooperative motions emerge naturally in inert particulate systems that exhibit close-packing, structural disorder, and glassy dynamics, such as colloidal glasses. A central feature that identifies these systems as being glassy is the slowing of internal structural rearrangement as system density is increased; with increasing system density, each particle becomes increasingly trapped by its neighbors so that, in order to rearrange at all, many neighboring particles must rearrange cooperatively. As such, the size of cooperative clusters increases as system density increases. Moreover, as size of the cluster grows the number of possible structural rearrangements decreases and, as such, the time needed for cooperative rearrangements increases precipitously until, eventually, the system becomes virtually frozen, or stuck.

Figure 12:
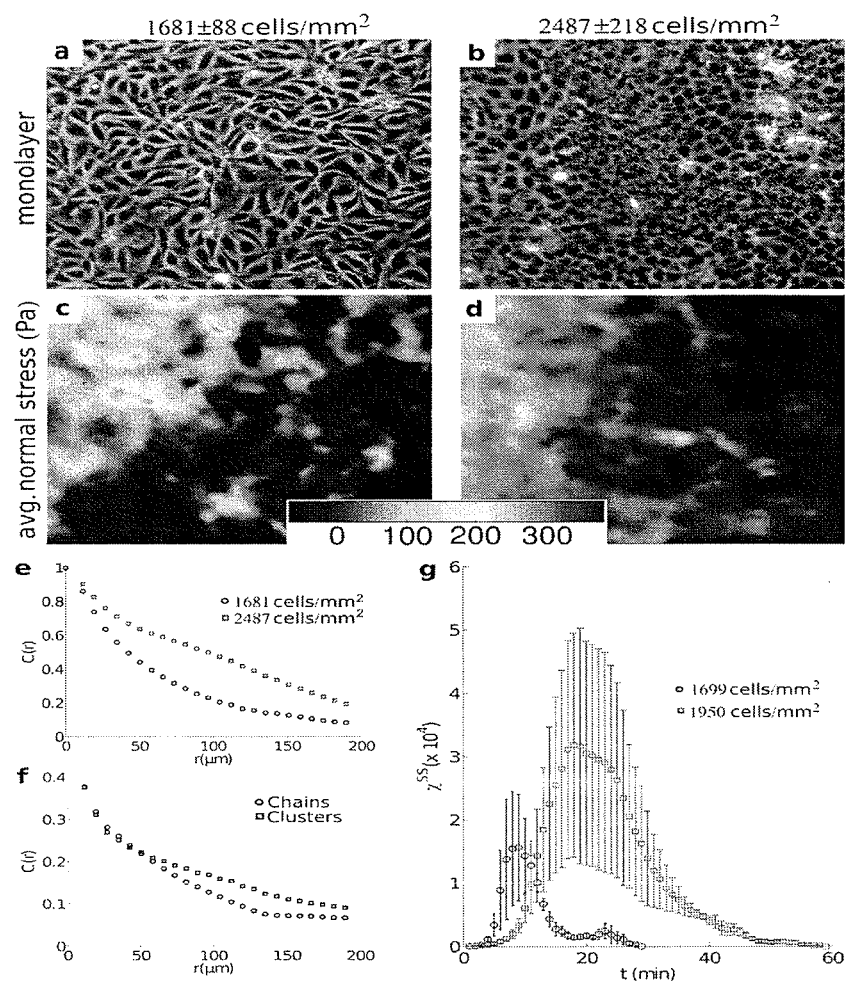
FIG. 12 includes phase contrast images and stress maps for Madin-Darby canine kidney (MDCK) cells showing effect of crowding of the cells on the intercellular stresses.

While cooperative cellular motions within the monolayer sheet exhibit these very signatures of glassy dynamics, to determine to what extent cellular stresses depict a complementary physical picture, the motion of the MDCK monolayers was analyzed as cellular density increased with the passage of time. Consistent with an expectation of glassy dynamics, the spatial decay in C(r) was smaller when the density was greater (FIG. 12(b), (d), and (e)), indicating that force cooperativity extended to greater distances. As a direct measure of slowing of structural rearrangements, metrics commonly used in soft condensed matter systems were used. The average number of cells which change position between two points in time defines an overlap function $q_s$:

$$q_s = \frac{1}{N} \sum_{1}^{N} w(|\vec{r}_i(t) - \vec{r}_i(t=0)|)$$

where the weight function w is equal to 1 if the distance between cell positions at sequential times is less than half a cell diameter, and zero otherwise. The variance of $q_s$ is then a measure of the rate of overall structural rearrangement and is related to the so-called four-point susceptibility $\chi^{ss}$ [26]. The peak in $\chi^{ss}$ occurs at the overall structural relaxation time, and the height of that peak is related to the size of rearranging regions[27, 28]. If the system is glassy, the peak in $\chi^{ss}$ is expected to shift towards longer times as system density is increased, and a clear shift of the peak in the more dense system confirms this expectation (FIG. 12(g)). The peak height also increases in the more dense system, confirming the presence of growing velocity clusters. Moreover, these density-dependent shifts in the position and the peak height of $\chi^{ss}$, which are indicative of slowing of structural rearrangements, occur simultaneously with growth of force clusters as indicated by the slowing decay in the force autocorrelation function with increasing density (FIG. 12(e)). Although a mechanistic link between inter-particle forces and spatially heterogeneous dynamics in glassy systems remains unclear, the findings illustrated in FIG. 12 are consistent with approach to a glass transition (further details regarding glass transition are provided, for example, in Supplement 9 of Exhibit B).

Recent advances have unraveled important features of stress transmission across specific molecular constituents of the focal adhesion and of the adherent junction, including vinculin, talin, and α-catenin for example, but the integrative context of these molecular events within integrated stress-bearing structures comprising highly redundant molecular pathways, or even across multi-cellular assemblies at larger scales of organization, have remained largely ambiguous. Logically, associated integrative principles have remained unstudied. Because distinct stress tensor components between contiguous cells in any complex living system have never before been measured, Monolayer Stress Microscopy now sets the study of underlying molecular events within an integrative mechanical context that is conceptually comprehensive and experimentally rigorous. The finding that each cell comprising a monolayer tends to migrate and remodel so as to maintain minimal local intercellular shear stress complements other integrative physiological principles (as further discussed Supplement 10 of Exhibit B).

A central question in morphogenesis and disease is how differentiated structures emerge from homogeneous cell populations. Differentiation and pattern formation in multicellular systems is currently explained by the existence of morphogenetic gradients and by local variations in the composition, topology, and stiffness of the extracellular matrix. In addition, once transduced by the sensory machinery of the individual cell, the spontaneously emergent rugged stress landscape described herein would be expected to trigger non-uniform secretion of soluble or insoluble factors, thus altering the local cellular microenviroment, causing cytoskeletal reinforcement or cytoskeletal fluidization, as well as activating in a highly non-uniform fashion stress-dependent genetic programs that give rise to differentiated tissues. These emergent stress heterogeneities are severe and persistent but unanticipated. How they might become harnessed and regulated during morphogenesis or repair and, perhaps more importantly, how they might become unharnessed or deregulated during disease or injury, remain open questions, but ones that are now accessible to direct experimental attack.

Some applications/uses based on determination of intercellular forces exerted within and between cells of a monolayer include:
   Wound healing (healing of scar, pulmonary fibrosis, performance of implants);
   Metastatic potential of cancer cells (all types of cancers, LAM);
   Permeability of endothelial/epithelial linings (atherosclerosis, blast injuries); and
   State of the intercellular binding (tissue integrity, pulmonary hypertension, damage due to inhaled pollution);

In all of the above applications, monolayer stress microscopy can be used to identify force hotspots, preferred loci of gap formation, invasive potential, and the ability for co-localization of molecular events with mechanical events. All of these are of great conceptual interest in connection with basic science as well as practical interest in connection with drug screening.

Applications/uses based on determination of intercellular forces exerted within and between cells of a monolayer further include performing medical diagnostic procedures, performing drug screening procedures, etc. Thus, for example, in some embodiments, a diagnostic method may be provided that includes placing a cellular monolayer sample on a substrate, determining traction forces exerted by the cellular monolayer sample on the substrate, determining internal forces (intercellular forces) within and between cells of the cellular monolayer based on the determined traction forces, and performing, based at least in part on the determined internal forces, a diagnostic procedure for the cellular monolayer sample to identify at least one condition in relation to the cellular monolayer sample. The at least one condition may include one or more of, for example, a cancerous condition, a vascular injury, a bladder dysfunction, and/or dysfunction of any barrier system in any monolayer. In some embodiment performing the diagnostic procedure may include, for example, performing a comparison of data representative of the determined internal forces within and between the cells of the cellular monolayer sample to data representative of determined internal forces within and between the cells of a healthy cellular monolayer specimen, and making a diagnosis of an existence of the at least one condition based on the comparison.

In some embodiments, a method for drug screening is provided that includes placing on a substrate a cellular monolayer sample, determining traction forces exerted on the substrate by the cellular monolayer sample, determining internal forces within and between cells of the cellular monolayer sample based on the determined traction forces, and performing a comparison of data representative of the determined internal forces within and between the cells of the cellular monolayer sample to data representative of determined internal forces within and between cells of a cellular monolayer specimen known to include a specified therapeutic substance (or, in some cases, to be free of such a specified therapeutic substance). A determination can then be made of whether the specified therapeutic substance is present in the cellular monolayer sample based on the comparison of data representative of the determined internal forces within and between the cells of the cellular monolayer sample to data representative of determined internal forces within and between cells of the cellular monolayer specimen known to include (or be free of) the specified therapeutic substance.

In further embodiments, a method for identifying an inhibitor of metastasis is provided that includes providing on a substrate a cellular monolayer sample, determining traction forces exerted on the substrate by the cellular monolayer sample in the presence of a candidate compound, and determining internal forces within and between cells of the cellular monolayer sample based on the determined traction forces. A first measure of determined internal forces within and between the cells of the cellular monolayer sample in the presence of said candidate compound is compared to a second measure of determined internal forces within and between cells of a cellular monolayer specimen in the absence of said candidate compound, wherein an alteration in the level of internal forces in the presence of the candidate compound compared to the absence of the candidate compound indicates that the compound inhibits metastasis.

Additional details regarding the determination of intercellular forces, analysis based on intercellular forces, and application involving or using intercellular forces, are provided below in Appendix A, B, and C.

Each of the various systems, apparatus, devices, components and modules used in the implementations described herein to perform the various operations required to process data acquired by a microscope relating to traction forces exerted by a monolayer and internal forces within and between cells of the monolayer may be implemented using processor-based systems that include a computer and/or other types of processor-based devices suitable for multiple applications. Such devices can include volatile and non-volatile memory elements, and peripheral devices to enable input/output functionality.

Figure 13:
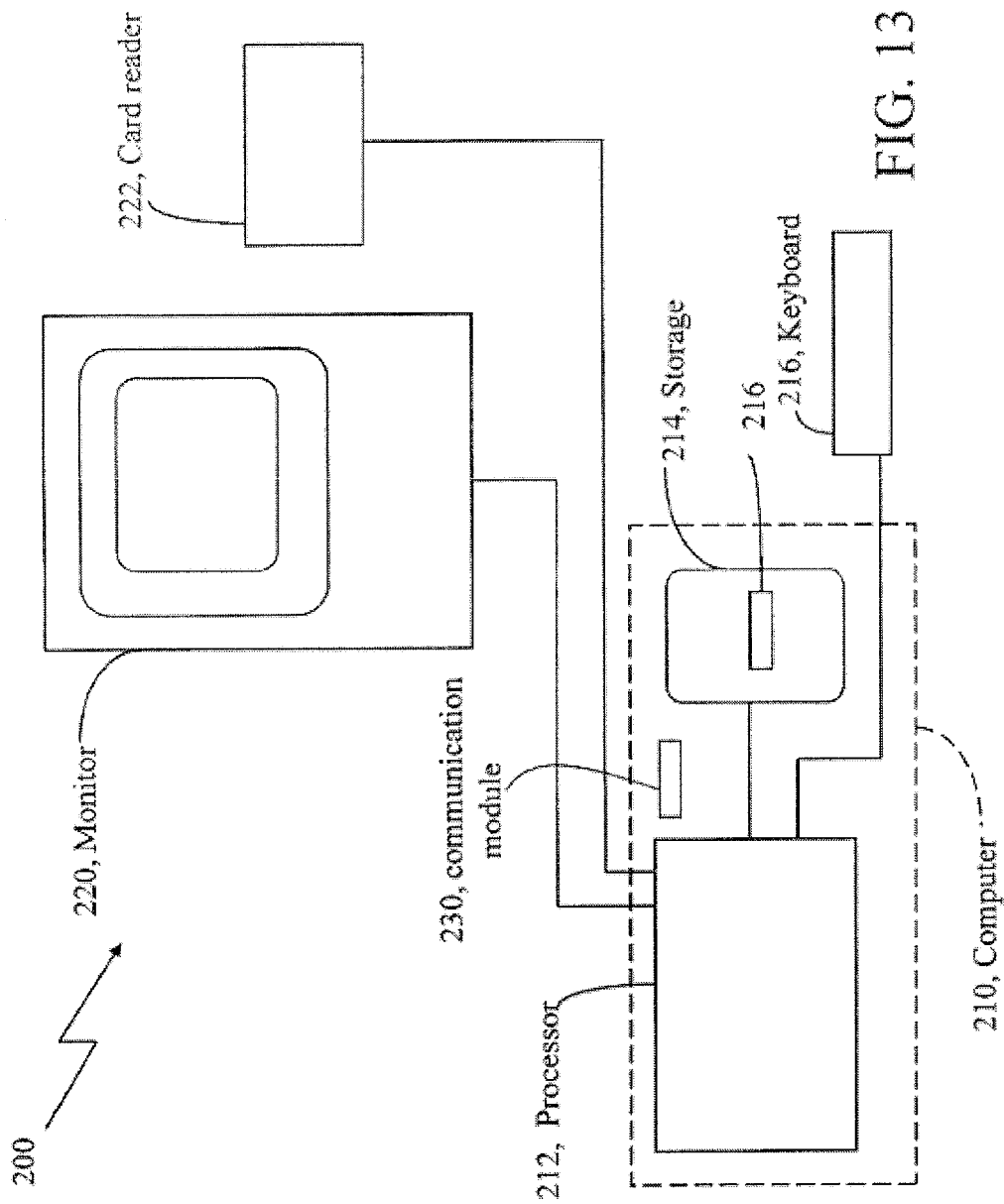
FIG. 13 is a schematic diagram of a generic computing system.

Specifically, with reference to FIG. 13, a schematic diagram of a generic computing system 200 that may be used to implement any of the processor-based systems required to process the data acquired for the purpose of determining traction and intercellular forces is shown. The computing system 200 includes a processor-based device 210 such as a personal computer, a specialized computing device, and so forth, that typically includes a central processor unit 212. In addition to the CPU 212, the system includes main memory, cache memory and bus interface circuits (not shown). The processor-based device 210 includes a mass storage element 214, such as a hard drive associated with the computer system. In some embodiments, the mass storage element 214 may be used to implement a data repository to record and maintain data such as, for example, image data and resultant processed data. The computing system 200 may further include a keyboard, or keypad, 216, and a monitor 220, e.g., a CRT (cathode ray tube) or LCD (liquid crystal display) monitor.

The processor-based device 210 is configured to facilitate, for example, the implementation of the processing of data to determine traction forces exerted by a cellular monolayer on a substrate, and to determine intercellular forces based on the traction forces. The storage device 214 may thus also include a computer program product that when executed on the processor-based device 210 causes the processor-based device to perform operations to facilitate the implementation of the data processing as described herein. The processor-based device may further include peripheral devices to enable input/output functionality. Such peripheral devices may include, for example, a CD-ROM drive and/or flash drive, or a network connection, for downloading related content to the connected system. Such peripheral devices may also be used for downloading software containing computer instructions to enable general operation of the respective system/device. Alternatively and/or additionally, in some embodiments, special purpose logic circuitry, e.g., an FPGA (field programmable gate array) or an ASIC (application-specific integrated circuit) may be used in the implementation of the system 200. Other modules that may be included with the processor-based device 210 are speakers, a sound card, a pointing device, e.g., a mouse or a trackball, by which the user can provide input to the computing system 200. The processor-based device 210 may include an operating system, e.g., Windows XP® Microsoft Corporation operating system. Alternatively, other operating systems could be used.

In further embodiments, a method for measuring stresses within a cell monolayer that is bigger than the optical field of view is provided that includes forming a specimen consisting of cell monolayer on gel and mounting firmly on an inverted microscope with automatic stage; defining a rectangular region around the monolayer with four corner points, for each corner x, y, and z coordinate is recorded such that the top layer of bead is in focus and the gel may have uniform thickness and may be mounted parallel to the stage guides with high accuracy; guiding the stage using the four corner coordinates to scan the entire rectangular plane and retrieve image tiles to cover the entire area with about 20% overlap between images; registering the images to form an entire image, the registration may be based on the minimum intensity difference in merged areas; calculating tractions as described in [Tambe et al, Nature Materials (2011), and Trepat et al, Nature Physics (2009)].

In further embodiments, a method for measuring stresses is provided that includes making an island statically determinate by removing rigid movements; allowing the remaining boundary to be traction free; and the remaining stress calculation procedure is described in [Tambe et al, Nature Materials (2011)].

Figure 16:
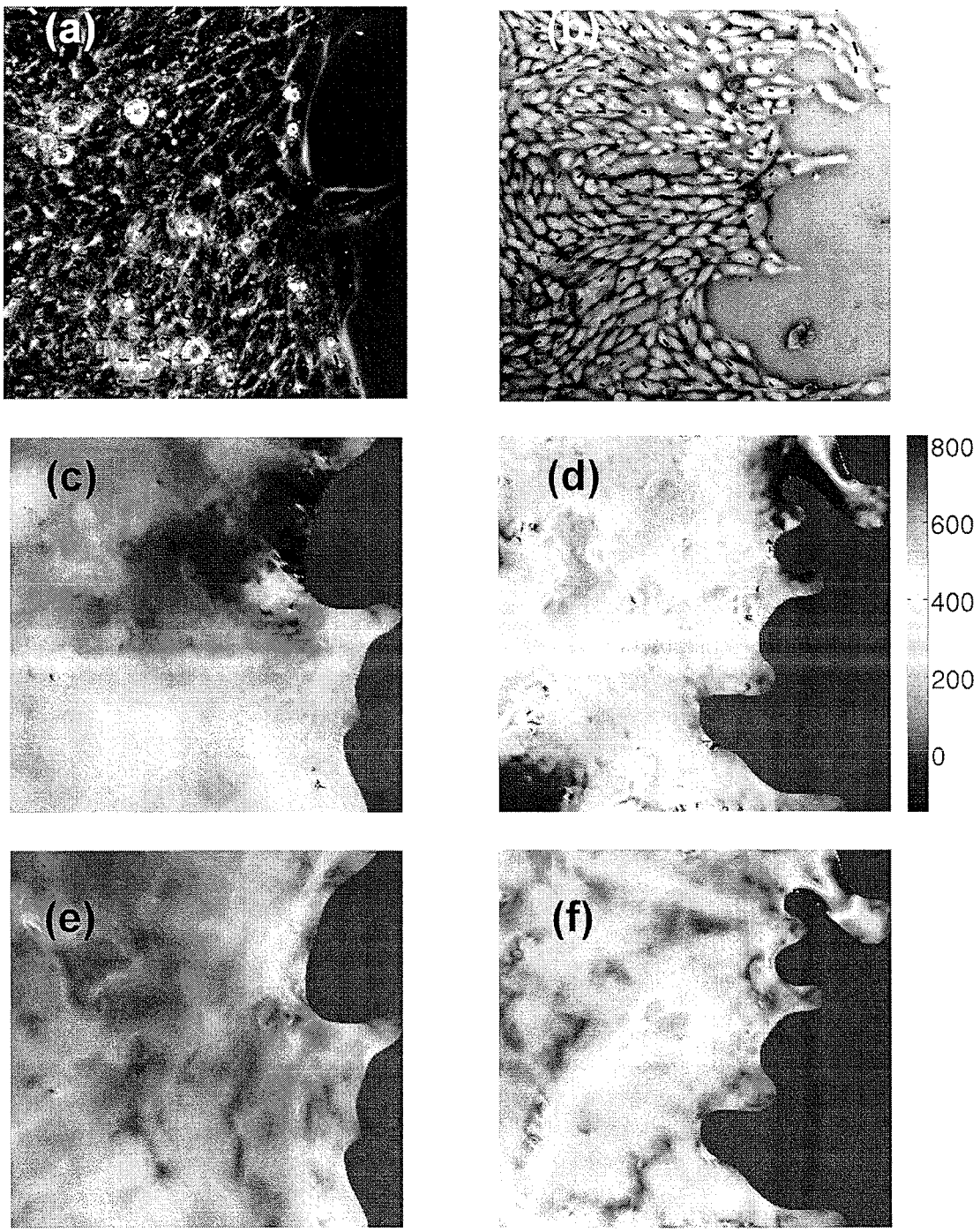
FIG. 16 is a series of plots showing that monolayer stresses can be used to detect a cell-cell junction defect present in certain cells from lymphangioleiomyomatosis (LAM) patients.

FIG. 16 is a series of plots showing an application of the current subject matter, specifically that intercellular stresses and specifically monolayer stresses as calculated by a method of the current subject matter detect a cell-cell junction defect present in certain cells from lymphangioleiomyomatosis (LAM) patients. Monolayer stresses bears signal of defective desmosomal junctions. FIG. 16 (*a*) shows kidney cells of patients with Bert-Hogg-Dube syndrome. Cells with this syndrome do not have folliculin (FLCN) proteins at localizes the desmosomal junctions. FIG. 16 (*b*) shows rescued cells that have normal levels of FLCN proteins. Absence of FLCN makes abnormal desmosomal cell-cell junctions. The measurements show bear signal of defective desmosomal junctions in the intercellular stresses.

Figure 17:
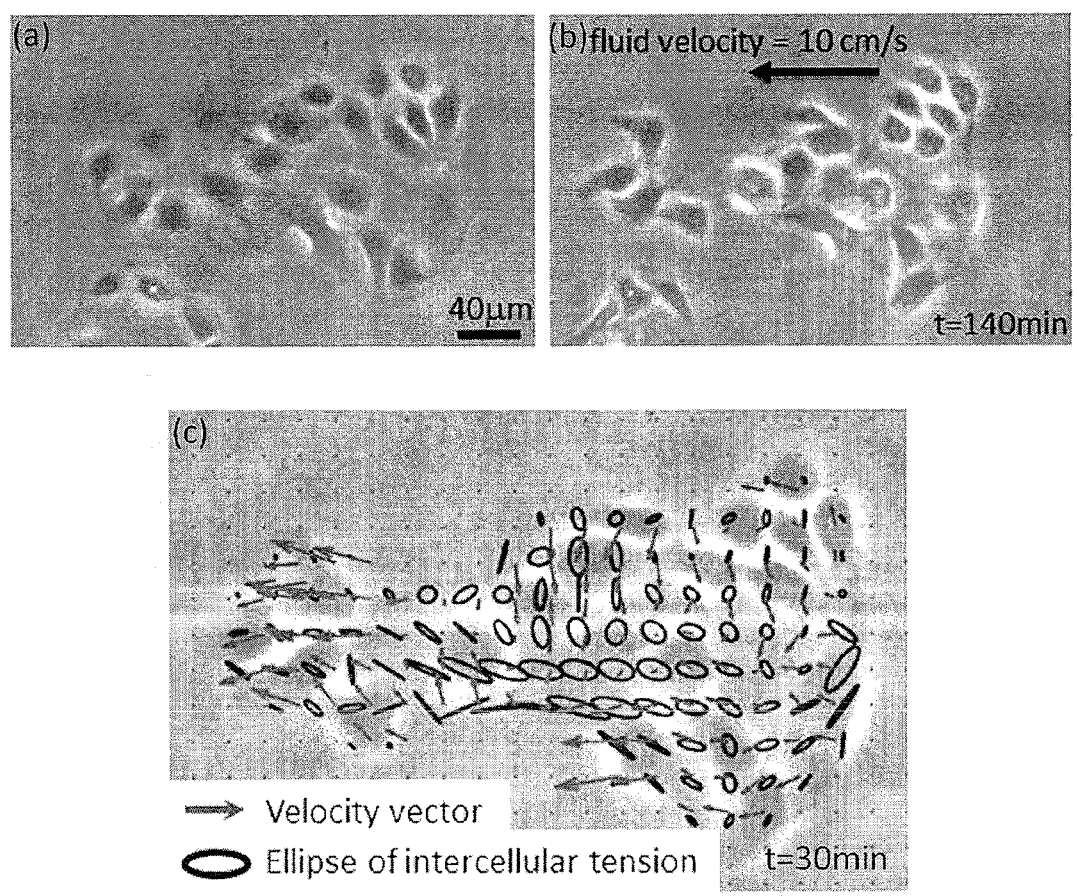
FIG. 17 is a series of plots showing analysis of shearing stress wherein fluid flows over the cells.

FIG. 17 is a series of plots showing analysis of shearing stress in accordance with a method of the current subject matter wherein fluid flows over the cells (thus creating a shearing stress). For example, intracellular stresses of endothelial tissues in blood vessels change in response to shear stress, and so those changes inform on cell mechanical communication. Monolayer stress microscopy (MSM) used to measure intercellular stresses in cells subjected to fluid shear stress. FIG. 17 (*a*) shows island of rat pulmonary microvascular endothelial (RPME) cells at time t=0. The cells are subjected to a steady flow of fluid on top surface, similar to flow of blood over cells lining blood vessels. FIG. 17 (*b*) shows the monolayer after 140 minutes of blood flow. FIG. 17 (*c*) shows arrows of local velocity vector and ellipse shows intercellular measured tension.

Figure 18:
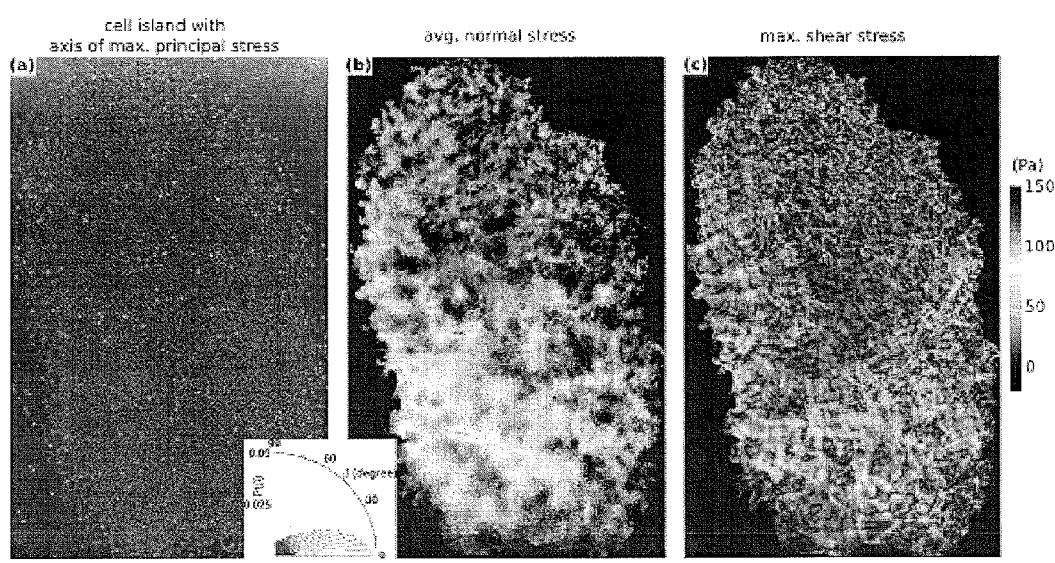
FIG. 18 is a series of plots illustrating a mapping of stresses in a cell monolayer that is larger than the field of view or in an entire monolayer.

FIG. 18 is a series of plots illustrating the mapping of stresses in a cell monolayer that is larger than the field of view or in an entire monolayer. The mechanical stresses within a RPME cell island are shown. FIG. 18 (*a*) shows a phase contrast image of the cell island overlaid with maximum principal orientation. Inset shows rose distribution of angle made by the maximum principal orientation with local cell orientation. FIG. 18 (*b*) shows a map of average normal stress. FIG. 18 (*c*) shows a map of maximum shear stress. The dimensions of the phase contrast image are height=4.5 mm and width=2.5 mm.

Figure 19:
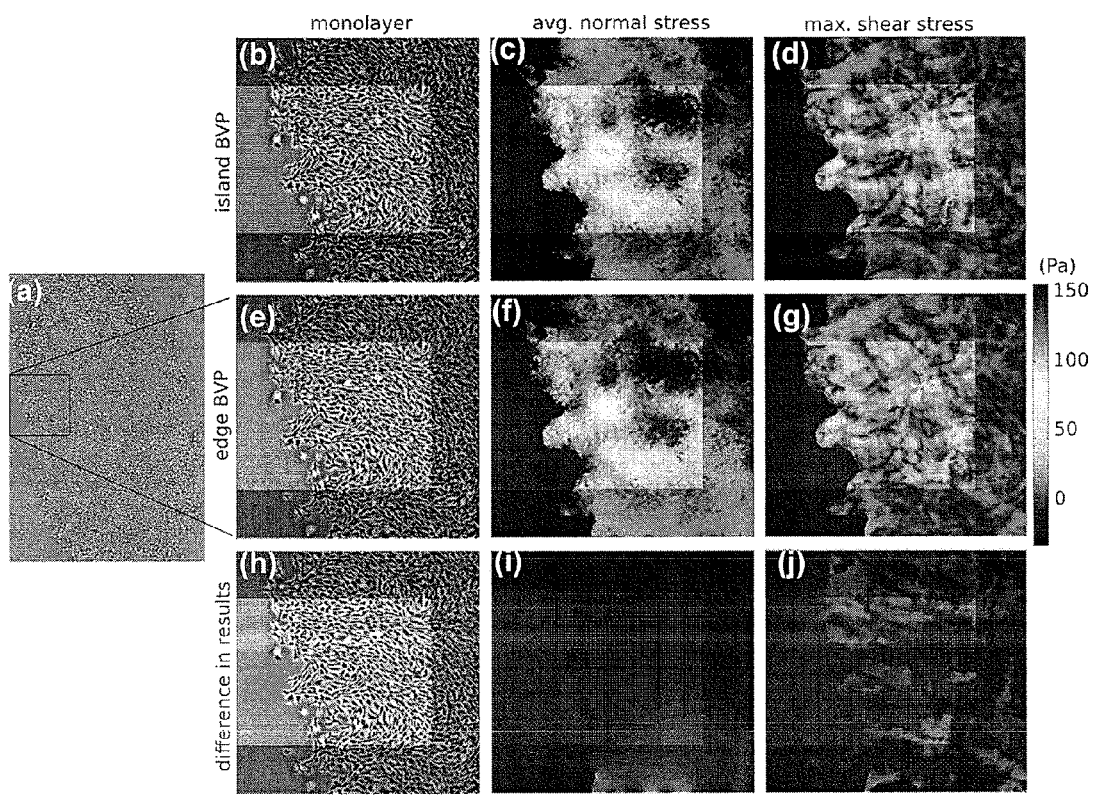
FIG. 19 is a series of plots illustrating the effect of boundary conditions.

FIG. 19 is a series of plots illustrating the effect of boundary conditions on a method of the current subject matter. Physical conditions imposed at the monolayer boundaries defined by optical field-of-view affect stresses away from the boundary but largely within 20% of length of the boundary. Effects of boundary conditions are obtained by comparing stresses in small regions of the cell island (see FIG. 19 (*a*)). Shaded regions in FIG. 19 (*b-j*) show region of width 20% of length of vertical boundary [See also Tambe 2011]. FIG. 19 (*b-d*) images show maximum principal orientation FIG. 19 (*b*), average normal stress FIG. 19 (*c*), and maximum shear stress FIG. 19 (*d*), in the small region shown. FIG. 19 (*e-g*) show similar maps. FIG. 19 (*h-j*) show a difference in results between FIG. 19 (*e-g*) and FIG. 19 (*b-d*).

Figure 20:
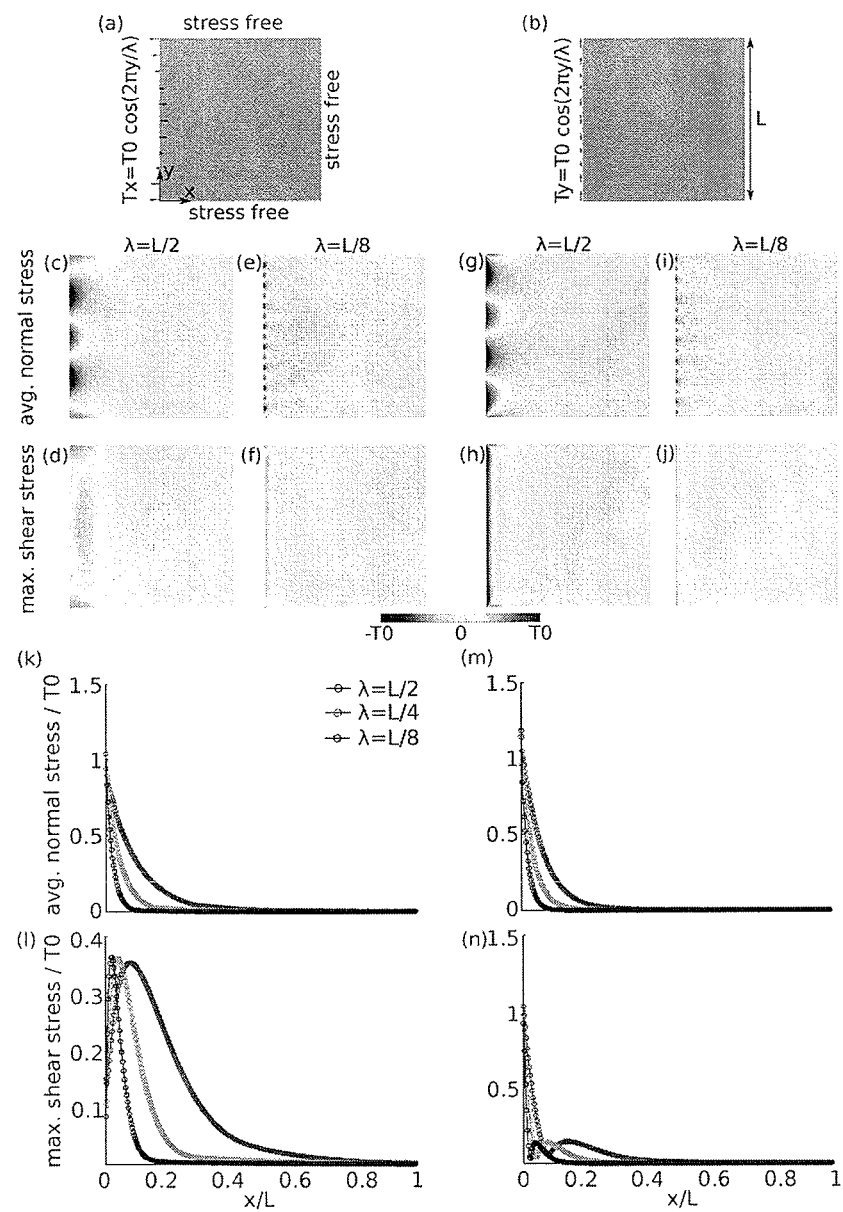
FIG. 20 is a series of plots also illustrating the effect of boundary conditions.

FIG. 20 is a series of plots illustrating the effect of boundary conditions on a method of the current subject matter. Artifacts in stresses decay exponentially as the distance from the boundary increases. The unknown tractions at the field-of-view boundary, from cells outside, may contain components normal as well as tangential to the boundary. The net error at the boundary will be a superposition of the two. Each component is analyzed separately by solving a boundary value problem where left edge is subjected to a fluctuating traction and the other edges do not have traction. The left half of FIG. 20 shows the effect of normal traction, and right half shows the effect of tangential traction. Both components of traction have avg. normal stress decay away from the loading FIG. 20 (*c, g*). As traction fluctuation frequency increases, the decay in average normal stress is faster FIG. 20 (*e, i*). Corresponding decay curves are shown in FIG. 20 (*k,m*). The decay of max shear stress away from the left edge is not monotonous FIG. 20 (*d,f,h,j*). FIG. 20 (*l,n*) show corresponding decay curves.

The various processor-based device used in conjunction with the implementations described herein may be connected using conventional network arrangements. For example, such processor-based devices may constitute part of a private packet-based network. Other types of network communication protocols may also be used to communicate between the various systems and systems/devices. Alternatively, the systems and devices may each be connected to network gateways that enable communication via a public network such as the Internet. Network communication links between the systems and devices may be implemented using wireless or wire-based links.

Various embodiments of the subject matter described herein may be realized in digital electronic circuitry, integrated circuitry, specially designed ASICs (application specific integrated circuits), computer hardware, firmware, software, and/or combinations thereof. These various embodiments may include embodiment in one or more computer programs that are executable and/or interpretable on a programmable system including at least one programmable processor, which may be special or general purpose, coupled to receive data and instructions from, and to transmit data and instructions to, a storage system, at least one input device, and at least one output device. Some embodiments include specific "modules" which may be implemented as digital electronic circuitry, integrated circuitry, specially designed ASICs (application specific integrated circuits), computer hardware, firmware, software, and/or combinations thereof.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any non-transitory computer program product, apparatus and/or device (e.g., magnetic discs, optical disks, memory, Programmable Logic Devices (PLDs)) used to provide machine instructions and/or data to a programmable processor, including a non-transitory machine-readable medium that receives machine instructions as a machine-readable signal.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback), and input from the user may be received in any form, including acoustic, speech, or tactile input.

Some or all of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an embodiment of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server generally arises by virtue of computer programs running on the respective computers and having a client-server relationship to each other.

Although particular embodiments have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the embodiments and features disclosed herein. Other unclaimed embodiments and features are also contemplated. Accordingly, other embodiments are within the scope of the following claims.

What is claimed is:

1. A method comprising:
    culturing a cellular monolayer on a deformable substrate, wherein the substrate includes a collagen coated polyacrylamide gel with fluorescent beads underneath a surface of the gel;
    determining, using a traction microscope, traction forces exerted by the cellular monolayer on the deformable substrate on which the monolayer is located; and
    determining internal forces within and between cells of the monolayer based on the determined traction forces,
    wherein the determining the traction forces includes:
        determining deformations of the substrate caused by the cellular monolayer, and
        determining the traction forces based on the determined deformations in the substrate;
    wherein determining the substrate deformation comprises:
        measuring the substrate deformation based on an acquired image pair, the image pair including one image of surface markers integrated with a surface of the substrate when the monolayer is placed on the substrate, and another image of the surface markers with the monolayer removed from the substrate;
        determining drift between of the surface markers based on the acquired image pair; and
        determining the deformations of the substrate at the surface based on data of the acquired image pair and based on the determined drift;
    wherein determining the drift comprises performing an a priori drift-correction technique based on fixed markers that are not displaced by deformations of the substrate due to the cellular monolayer.

2. The method of claim 1, wherein determining the internal forces of the cellular monolayer based on the determined traction forces comprises:
    determining internal stresses within the cellular monolayer that act to balance the determined traction forces over at least part of the cellular monolayer.

3. The method of claim 2, wherein determining the internal stresses that act to balance the determined traction forces over the at least part of the monolayer comprises:
    determining the internal stresses resulting from imposing mechanical equilibrium of forces according to $\sigma_{ij,i}=T_i$, where $\sigma_{ij}$ represents internal stress within the cellular monolayer, and at a same position, $T_i$ represents a traction force exerted by the cells on the substrate;
    setting boundary conditions at a boundary determined based on an optical field of view of an observed section of the monolayer;
    determining errors associated with the setting of the boundary conditions; and
    identifying an inner region where the determined errors are smaller than a pre-determined error threshold.

4. The method of claim 3, wherein setting the boundary conditions at the boundary determined based on the optical field of view comprises:
    setting the boundary conditions along the optical field of view when a region within the boundary does not include a free edge of the monolayer; and
    setting the boundary conditions along an edge defined by sides of a group of cells that do not abut sides of another group of cells from the monolayer when the optical field of view includes free edges of the monolayer.

5. The method of claim 3, wherein setting the boundary conditions comprises:
setting the boundary conditions at the boundary to have one or more of: a zero normal displacement, zero stress, and any given relationship between displacement and stress.

6. The method of claim 3, wherein determining the internal stresses resulting from imposing mechanical equilibrium of the forces according to $\sigma_{ij,i}=T_i$ comprises:
performing one or more numerical techniques to solve equations of the mechanical equilibrium over a mathematical representation of the at least part of the cellular monolayer subjected to the traction forces using boundary conditions set along one or more of: the optical field of view, and free edges of the monolayer.

7. The method of claim 1, wherein determining deformations of the substrate comprises:
applying a numerical technique to a drift corrected image pair to obtain the deformations of the substrate at the surface.

8. The method of claim 7, wherein applying the numerical technique comprises:
applying a cross-correlation numerical technique to the drift corrected image pair.

9. The method of claim 1, wherein determining the traction forces based on the determined deformations in the substrate comprises:
performing a traction microscopy procedure on data representative of the deformations in the substrate caused by the traction forces exerted by the cellular monolayer on the substrate to determine the traction forces.

10. The method of claim 9, wherein performing the traction microscopy procedure comprises:
applying a Fourier-Transform-based procedure to transform the deformations of the substrate into tractions on a surface of the substrate.

11. A method comprising:
culturing a cellular monolayer on a deformable substrate, wherein the substrate includes a collagen coated polyacrylamide gel with fluorescent beads underneath a surface of the gel;
determining, using a traction microscope, traction forces exerted by the cellular monolayer on the deformable substrate on which the monolayer is located; and
determining internal forces within and between cells of the monolayer based on the determined traction forces, wherein determining the internal forces of the cellular monolayer based on the determined traction forces comprises:
determining internal stresses within the cellular monolayer that act to balance the determined traction forces over at least part of the cellular monolayer;
wherein determining the internal stresses that act to balance the determined traction forces over the at least part of the monolayer comprises:
determining the internal stresses resulting from imposing mechanical equilibrium of forces according to $\sigma_{ij,i}=T_i$ where $\sigma_{ij}$ represents internal stress within the cellular monolayer, and at a same position, $T_i$ represents a traction force exerted by the cells on the substrate;
setting boundary conditions at a boundary determined based on an optical field of view of an observed section of the monolayer; wherein setting the boundary conditions at the boundary determined based on the optical field of view comprises:
setting the boundary conditions along the optical field of view when a region within the boundary does not include a free edge of the monolayer; and setting the boundary conditions along an edge defined by sides of a group of cells that do not abut sides of another group of cells from the monolayer when the optical field of view includes free edges of the monolayer;
determining errors associated with the setting of the boundary conditions; and
identifying an inner region where the determined errors are smaller than a pre-determined error threshold.

12. The method of claim 11, wherein setting the boundary conditions comprises:
setting the boundary conditions at the boundary to have one or more of: a zero normal displacement, zero stress, and any given relationship between displacement and stress.

13. The method of claim 11, wherein determining the internal stresses resulting from imposing mechanical equilibrium of the forces according to $\sigma_{ij,i}=T_i$ comprises:
performing one or more numerical techniques to solve equations of the mechanical equilibrium over a mathematical representation of the at least part of the cellular monolayer subjected to the traction forces using boundary conditions set along one or more of: the optical field of view, and free edges of the monolayer.

* * * * *